(12) United States Patent
Niyaz et al.

(10) Patent No.: US 9,131,694 B2
(45) Date of Patent: Sep. 15, 2015

(54) INSECTICIDAL PYRIDINE COMPOUNDS

(71) Applicant: Dow AgroSciences, LLC, Indianapolis, IN (US)

(72) Inventors: Noormohamed M. Niyaz, Indianapolis, IN (US); Francis E. Tisdell, Carmel, IN (US); Gerald B. Watson, Zionsville, IN (US); James M. Renga, Indianapolis, IN (US); William C. Lo, Fishers, IN (US); Maurice C. H. Yap, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/070,254

(22) Filed: Nov. 1, 2013

(65) Prior Publication Data

US 2014/0141975 A1   May 22, 2014

Related U.S. Application Data

(62) Division of application No. 12/799,478, filed on Apr. 26, 2010, now Pat. No. 8,604,199.

(60) Provisional application No. 61/172,958, filed on Apr. 27, 2009.

(51) Int. Cl.

| | | |
|---|---|---|
| *C07D 413/14* | (2006.01) | |
| *A01N 43/76* | (2006.01) | |
| *A01N 43/40* | (2006.01) | |
| *A01N 55/00* | (2006.01) | |
| *C07D 401/14* | (2006.01) | |

(52) U.S. Cl.
CPC ............... *A01N 43/76* (2013.01); *A01N 43/40* (2013.01); *A01N 55/00* (2013.01); *C07D 401/14* (2013.01); *C07D 413/14* (2013.01)

(58) Field of Classification Search
CPC ...................................................... C07D 413/14
USPC .......................................... 546/256; 514/333
See application file for complete search history.

(56) References Cited

U.S. PATENT DOCUMENTS

| | | | |
|---|---|---|---|
| 4,474,599 A | 10/1984 | Rogers et al. | |
| 5,084,459 A | 1/1992 | Uneme et al. | |
| 5,723,450 A | 3/1998 | Reuschling et al. | |
| 5,994,373 A | 11/1999 | Olesen | |
| 6,004,977 A | 12/1999 | Kurys et al. | |
| 6,878,726 B2 | 4/2005 | Cheng et al. | |
| 7,087,616 B2 | 8/2006 | Fischer et al. | |
| 7,119,098 B2 | 10/2006 | Nagarajan et al. | |
| 7,238,697 B2 | 7/2007 | Bretschneider et al. | |
| 7,371,759 B2 | 5/2008 | Ahmad et al. | |

FOREIGN PATENT DOCUMENTS

| | | |
|---|---|---|
| DE | 10/2008/000872 | 11/2008 |
| EP | 1273580 A1 | 1/2003 |
| EP | 1775293 A1 | 4/2007 |
| EP | 1783114 A1 | 5/2007 |
| WO | 2005/063736 | 7/2005 |
| WO | 2009/025823 A1 | 1/2009 |

OTHER PUBLICATIONS

U.S. Appl. No. 12/799,478, filed Apr. 26, 2010, Niyaz et al.
European Patent Office. Patent Cooperation Treaty International Search Report and Written Opinion of the International Searching Authority. PCT Patent Application No. PCT/US2010/001232. Jul. 28, 2010.
Allan, J.R; Paton, A.D. Preparation, structural characterisation, thermal and electrical studies of some first row transition metal complexes of 2,3-bis(2-pyridyl)pyrazine. Thermochimica Acta, 214 (1993), pp. 227-233.
Katritzky, A.R.; Jiang, J.; Greenhill, J.V. 1,2- and 1,3- Monoazabisylides as Novel Synthones. Journal of Organic Chemistry, 1993, vol. 58, pp. 1987-1988.
Heirtzler, F.; Neuburger, M.; Kulike, K. Insights on the synthesis and organisational phenomena of twisted pyrazine-pyridine hybrids. J. Chem. Soc., Perkin Trans. 1, 2002. p. 809-820.
Sumengen, D. The Preparation of 3, 4-Diaryl Furoxans and 3,5-diaryl-1,2,4-Oxadiazol-4-Oxides. Chimica Acta Turcica 13 (1985), pp. 3939-402.
Colonna, M,; Risaliti, A. Recerche sugli azocomosti N-eterociclici.—Nota VIII. Reazione con difenilchetene ed autossidazione degli addotti da azoici simmetrici. Gassetta Chimica Italiana, Societa Chimica, Italiana, Rome; Italy. vol. 90, Jan. 1, 1960, pp. 1165-1178.
International Preliminary Report on Patentability, PCT/US2010/001232, Apr. 26, 2010, Dow AgroSciences, LLC.
Dorwald, Side Reactions in Organic Synthesis, 2005, Wiley: VCH Weinheim Preface, pp. 1-15 & Chapter 8, pp. 279-308.

*Primary Examiner* — Patricia L. Morris
(74) *Attorney, Agent, or Firm* — Carl D. Corvin; Maschoff Brennan

(57) ABSTRACT

The invention disclosed in this document is related to the field of pesticides and their use in controlling pests. Novel pyridine compounds for use in controlling pests are disclosed.

11 Claims, No Drawings

INSECTICIDAL PYRIDINE COMPOUNDS

CROSS REFERENCE TO RELATED APPLICATIONS

The present application is a divisional of U.S. patent application Ser. No. 12/799,478 filed 26 Apr. 2009, now U.S. Pat. No. 8,604,199, which claims priority to U.S. Provisional Patent Application No. 61/172,958 filed 27 Apr. 2009. The contents of these applications are incorporated herein by reference in their entirety.

FIELD OF THE INVENTION

The inventions disclosed in this document are related to the field of pesticides and their use in controlling pests.

BACKGROUND

Pests cause millions of human deaths around the world each year. Furthermore, there are more than ten thousand species of pests that cause losses in agriculture. These agricultural losses amount to billions of U.S. dollars each year. Termites cause damage to various structures such as homes. These termite damage losses amount to billions of U.S. dollars each year. As a final note, many stored food pests eat and adulterate stored food. These stored food losses amount to billions of U.S. dollars each year, but more importantly, deprive people of needed food.

There is an acute need for new pesticides. Insects are developing resistance to pesticides in current use. Hundreds of insect species are resistant to one or more pesticides. The development of resistance to some of the older pesticides, such as DDT, the carbonates, and the organophosphates, is well known. But resistance has even developed to some of the newer pesticides. Therefore, a need exists for new pesticides and particularly for pesticides that have new modes of action.

SUMMARY

This invention concerns compounds useful for the control of insects, especially useful for the control of aphids and other sucking insects. More specifically, the invention concerns compounds of formula I:

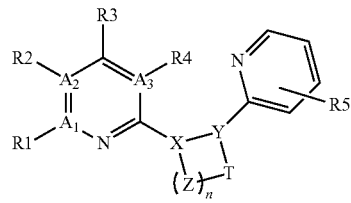

wherein A1, A2, A3, X, Y, Z, T, n, R1, R2, R3, R4, R5, R6 and R7 are as defined herein.

The invention also provides new processes for preparing compounds of formula I as well as new compositions and methods of use, which will be described in detail hereinafter. Further embodiments, forms, aspects, features, and details of the present invention shall become apparent from the descriptions contained herein.

DETAILED DESCRIPTION

The compounds of this application have the following molecular structure:

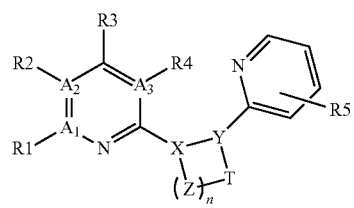

Formula (I)

wherein
A1, A2, and A3, are each independently C or N, with the proviso that A1 and A2 are not simultaneously N;
X and Y are independently C or N;
Z and T are each independently $C(R6)_2$ (where R6 could be the same or different), C=O, C=NR7, NR7, O, S(O)n' (n'=0-2);
n=0, 1, 2 and 3 (X, Y, T and Z together form a 3- or 4- or 5- or 6-membered heteroaryl or a fully or partially saturated heterocyclic ring);
R1 is (provided that A1 is not N) H, CN, CHO, —SCN, $NO_2$, F, Cl, Br, I, substituted or unsubstituted C1-C4-alkyl, substituted or unsubstituted halo-C1-C4-alkyl, substituted or unsubstituted C1-C4-alkoxy, substituted or unsubstituted halo-C1-C4-alkoxy, substituted or unsubstituted C1-C4-thioalkyl, substituted or unsubstituted halo-C1-C4-thioalkyl, substituted or unsubstituted C3-C7-cycloalkyl, substituted or unsubstituted C2-C4-alkenyl, C2-C4-alkynyl, substituted or unsubstituted C1-C4-acylalkyl, C1-C4-acyloxy, C1-C4 alkoxycarbonyl, C1-C4-alkoxy-amino, C1-C4-alkyl-S(O)=NH, substituted or unsubstituted aryl, substituted or unsubstituted heterocyclyl, wherein the substituents are one or more of the following F, C1, Br, OH, CN, $NO_2$, CHO, —SCN, S(O)n-C1-C4-alkyl (where n=0-2), C1-C4-alkyl, halo-C1-C4-alkyl, C1-C4-alkylamine, C1-C4-alkoxy, halo-C1-C4-alkoxy, C1-C4-thioalkyl, halo-C1-C4-thioalkyl, C1-C4-alkylacyl, C1-C4-acyloxy, C1-C4 alkoxycarbonyl, C1-C4-alkoxy-imino, hydroxy-imino, C1-C4-alkyl-S(O)=NH, (C1-C4-trialkyl)Si;
R2 is (provided that A2 is not N) H, CN, CHO, —SCN, $NO_2$, F, C1, Br, I, substituted or unsubstituted C1-C4-alkyl, substituted or unsubstituted halo-C1-C4-alkyl, substituted or unsubstituted C1-C4-alkoxy, substituted or unsubstituted halo-C1-C4-alkoxy, substituted or unsubstituted C1-C4-thioalkyl, substituted or unsubstituted halo-C1-C4-thioalkyl, substituted or unsubstituted C3-C7-cycloalkyl, substituted or unsubstituted C2-C4-alkenyl, C2-C4-alkynyl, substituted or unsubstituted C1-C4-acylalkyl, C1-C4-acyloxy, C1-C4 alkoxycarbonyl, C1-C4-alkoxy-amino, C1-C4-alkyl-S(O)=NH, substituted or unsubstituted aryl, substituted or unsubstituted heterocyclyl, wherein the substituents are one or more of the following F, C1, Br, OH, CN, $NO_2$, CHO, —SCN, S(O)n-C1-C4-alkyl (where n=0-2), C1-C4-alkyl, halo-C1-C4-alkyl, C1-C4-alkylamine, C1-C4-alkoxy, halo-C1-C4-alkoxy, C1-C4-thioalkyl, halo-C1-C4-thioalkyl, C1-C4-alkylacyl, C1-C4-acyloxy, C1-C4 alkoxycarbonyl, C1-C4-alkoxy-imino, hydroxy-imino, C1-C4-alkyl-S(O)=NH, (C1-C4-trialkyl)Si;
R3 is CN, $NO_2$, F, Cl, Br, I, substituted or unsubstituted halo-C1-C4-alkyl, or unsubstituted C3-C7-cycloalkyl, substituted or unsubstituted halo-C1-C4-alkoxy, substituted or unsubstituted halo-C1-C4-thioalkyl substituted or unsubstituted halo-C2-C4-alkenyl, substituted or unsubstituted five membered heteroaryl, wherein the substituents are one or more of the following F, Cl, Br, OH, CN, $NO_2$, CHO, —SCN, S(O)n-C1-C4-alkyl (where n=0-2), C1-C4-alkyl, halo-C1-

C4-alkyl, C1-C4-alkylamine, C1-C4-alkoxy, halo-C1-C4-alkoxy, C1-C4-thioalkyl, halo-C1-C4-thioalkyl, C1-C4-alkylacyl, C1-C4-acyloxy, C1-C4 alkoxycarbonyl, C1-C4-alkoxy-imino, hydroxy-imino, C1-C4-alkyl-S(O)=N;

R4 is (provided that A3 is not N) H, CN, CHO, —SCN, $NO_2$, F, Cl, Br, I, substituted or unsubstituted C1-C4-alkyl, substituted or unsubstituted halo-C1-C4-alkyl, substituted or unsubstituted C1-C4-alkoxy, substituted or unsubstituted halo-C1-C4-alkoxy, substituted or unsubstituted C1-C4-thioalkyl, substituted or unsubstituted halo-C1-C4-thioalkyl, substituted or unsubstituted C3-C7-cycloalkyl, substituted or unsubstituted C2-C4-alkenyl, C2-C4-alkynyl, substituted or unsubstituted C1-C4-acylalkyl, C1-C4-acyloxy, C1-C4 alkoxycarbonyl, C1-C4-alkoxy-amino, C1-C4-alkyl-S(O)=NH, substituted or unsubstituted aryl, substituted or unsubstituted heterocyclyl, wherein the substituents are one or more of the following F, Cl, Br, OH, CN, $NO_2$, CHO, —SCN, S(O)n-C1-C4-alkyl (where n=0-2), C1-C4-alkyl, halo-C1-C4-alkyl, C1-C4-alkylamine, C1-C4-alkoxy, halo-C1-C4-alkoxy, C1-C4-thioalkyl, halo-C1-C4-thioalkyl, C1-C4-alkylacyl, C1-C4-acyloxy, C1-C4 alkoxycarbonyl, C1-C4-alkoxy-imino, hydroxy-imino, C1-C4-alkyl-S(O)=NH, (C1-C4-trialkyl)Si:

R5 is H, CN, CHO, —SCN. $NO_2$, F, Cl, Br, I, substituted or unsubstituted C1-C4-alkyl, substituted or unsubstituted halo-C1-C4-alkyl, substituted or unsubstituted C1-C4-alkoxy, substituted or unsubstituted halo-C1-C4-alkoxy, substituted or unsubstituted C1-C4-thioalkyl, substituted or unsubstituted halo-C1-C4-thioalkyl, substituted or unsubstituted C3-C7-cycloalkyl, substituted or unsubstituted C2-C4-alkenyl, C2-C4-alkynyl, substituted or unsubstituted C1-C4-acylalkyl, C1-C4-acyloxy, C1-C4 alkoxycarbonyl, C1-C4-alkoxy-amino, C1-C4-alkyl-S(O)=NH, substituted or unsubstituted aryl, substituted or unsubstituted heterocyclyl, wherein the substituents are one or more of the following F, Cl, Br, OH, CN, $NO_2$, CHO, —SCN, S(O)n-C1-C4-alkyl (where n=0-2), C1-C4-alkyl, halo-C1-C4-alkyl, C1-C4-alkylamine, C1-C4-alkoxy, halo-C1-C4-alkoxy, C1-C4-thioalkyl, halo-C1-C4-thioalkyl, C1-C4-alkylacyl, C1-C4-acyloxy, C1-C4 alkoxycarbonyl, C1-C4-alkoxy-imino, hydroxy-imino, C1-C4-alkyl-S(O)=NH, (C1-C4-trialkyl)Si;

R6 is H, OH, SH, CN, CHO, —SCN, $NO_2$, F, Cl, Br, I, substituted or unsubstituted C1-C4-alkyl, substituted or unsubstituted halo-C1-C4-alkyl, substituted or unsubstituted C1-C4-alkoxy, substituted or unsubstituted halo-C1-C4-alkoxy, substituted or unsubstituted C1-C4-thioalkyl, substituted or unsubstituted halo-C1-C4-thioalkyl, substituted or unsubstituted C3-C7-cycloalkyl, substituted or unsubstituted C2-C4-alkenyl, C2-C4-alkynyl, substituted or unsubstituted C1-C4-acylalkyl, C1-C4-acyloxy, C1-C4 alkoxycarbonyl, C1-C4-alkyl-S(O)=NH, substituted or unsubstituted aryl, substituted or unsubstituted heterocyclyl, wherein the substituents are one or more of the following F, Cl, Br, OH, CN, $NO_2$, CHO, —SCN, S(O)n-C1-C4-alkyl (where n=0-2), C1-C4-alkyl, halo-C1-C4-alkyl, C1-C4-alkylamine, C1-C4-alkoxy, halo-C1-C4-alkoxy, C1-C4-thioalkyl, halo-C1-C4-thioalkyl, C1-C4-alkylacyl, C1-C4-acyloxy, C1-C4 alkoxycarbonyl, C1-C4-alkoxy-imino, hydroxy-imino, C1-C4-alkyl-S(O)=NH, (C1-C4-trialkyl)Si; and R7 is H, OH, CN, NH2, CHO, —SCN, $NO_2$, substituted or unsubstituted C1-C4-alkyl, substituted or unsubstituted halo-C1-C4-alkyl, substituted or unsubstituted C1-C4-alkoxy, substituted or unsubstituted halo-C1-C4-alkoxy, substituted or unsubstituted C1-C4-alkylamine, substituted or unsubstituted C1-C4-thioalkyl, substituted or unsubstituted halo-C1-C4-thioalkyl, substituted or unsubstituted C3-C7-cycloalkyl, substituted or unsubstituted C2-C4-alkenyl, substituted or unsubstituted C1-C4-acylalkyl, C1-C4-acyloxy, C1-C4 alkoxycarbonyl, C1-C4-alkyl-S(O)=NH, substituted or unsubstituted aryl, substituted or unsubstituted heterocyclyl, wherein the substituents are one or more of the following F, Cl, Br, OH, CN, $NO_2$, CHO, —SCN, S(O)n-C1-C4-alkyl (where n=0-2), C1-C4-alkyl, halo-C1-C4-alkyl, C1-C4-alkylamine, C1-C4-alkoxy, halo-C1-C4-alkoxy, C1-C4-thioalkyl, halo-C1-C4-thioalkyl, C1-C4-alkylacyl, C1-C4-acyloxy, C1-C4 alkoxycarbonyl, C1-C4-alkoxy-imino, hydroxy-imino, C1-C4-alkyl-S(O)=NH, (C1-C4-trialkyl)Si.

Substituents (Non-Exhaustive List)

The examples given for the substituents are (except for halo) non-exhaustive and must not be construed as limiting the invention disclosed in this document.

"alkenyl" means an acyclic, unsaturated (at least one carbon-carbon double bond), branched or unbranched, substituent consisting of carbon and hydrogen, for example, vinyl, allyl, butenyl, pentenyl, hexenyl, heptenyl, octenyl, nonenyl, and decenyl.

"alkoxy" means an alkyl further consisting of a carbon-oxygen single bond, for example, methoxy, ethoxy, propoxy, isopropoxy, 1-butoxy, 2-butoxy, isobutoxy, tert-butoxy, pentoxy, 2-methylbutoxy, 1,1-dimethylpropoxy, hexoxy, heptoxy, octoxy, nonoxy, and decoxy.

"alkyl" means an acyclic, saturated, branched or unbranched, substituent consisting of carbon and hydrogen, for example, methyl, ethyl, propyl, isopropyl, 1-butyl, 2-butyl, isobutyl, tert-butyl, pentyl, 2-methylbutyl, 1,1-dimethylpropyl, hexyl, heptyl, octyl, nonyl, and decyl.

"alkynyl" means an acyclic, unsaturated (at least one carbon-carbon triple bond, and any double bonds), branched or unbranched, substituent consisting of carbon and hydrogen, for example, ethynyl, propargyl, butynyl, pentynyl, hexynyl, heptynyl, octynyl, nonynyl, and decynyl.

"aryl" means a cyclic, aromatic substituent consisting of hydrogen and carbon, for example, phenyl, naphthyl, and biphenylyl.

"cycloalkyl" means a monocyclic or polycyclic, saturated substituent consisting of carbon and hydrogen, for example, cyclopropyl, cyclobutyl, cyclopentyl, cyclohexyl, cycloheptyl, cyclooctyl, cyclodecyl, norbornyl, bicyclo[2.2.2]octyl, and decahydronaphthyl.

"halo" means fluoro, chloro, bromo, and iodo.

"haloalkyl" means an alkyl further consisting of, from one to the maximum possible number of, identical or different, halos, for example, fluoromethyl, difluoromethyl, trifluoromethyl, 1-fluoromethyl, 2-fluoroethyl, 2,2,2-trifluoroethyl, chloromethyl, trichloromethyl, and 1,1,2,2-tetrafluoroethyl.

"heterocyclyl" means a cyclic substituent that may be fully saturated, partially unsaturated, or fully unsaturated, where the cyclic structure contains at least one carbon and at least one heteroatom, where said heteroatom is nitrogen, sulfur, or oxygen, for example, benzofuranyl, benzoisothiazolyl, benzoisoxazolyl, benzoxazolyl, benzothienyl, benzothiazolyl cinnolinyl, furanyl, indazolyl, indolyl, imidazolyl, isoindolyl, isoquinolinyl, isothiazolyl, isoxazolyl, 1,3,4 oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, 1,2,3,4-tetrazolyl, thiazolinyl, thiazolyl, thienyl, 1,2,3-triazinyl, 1,2,4-triazinyl, 1,3,5-triazinyl, 1,2,3-triazolyl, and 1,2,4-triazolyl.

SYNTHESIS SCHEMES (NON-EXHAUSTIVE LIST)

Compounds of the formula (I) can be prepared according to the following methods.

Method 1

Scheme [1]

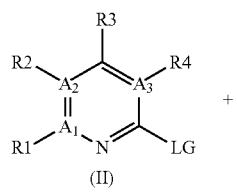

+

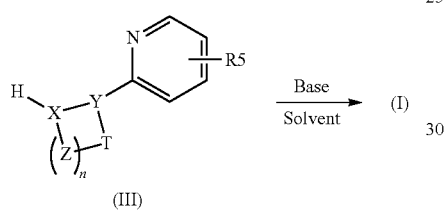

Compounds of the formula (I) can be prepared by treating compounds of the formula (II), where LG is a halogen (F, Cl, Br, I) or a sulfone or other leaving group and R1, R2, R3, R4, A1, A2 and A3 are as defined above, and compounds of the formula (III), where R5, X, Y, Z and T are as defined above, in an aprotic or protic solvent in the presence of a stoicheometric or catalytic amount of a base at a temperature between −20 and 250° C. (heating under conventional or in a microwave reactor) and at a pressure (0-300 psi) (Scheme 1). Suitable solvents, include, but are not limited to, water, tetrahydrofuran, 1,4-dioxane, dimethylformamide, dimethylsulfoxide, acetonitrile, chloroform, methylene chloride, and mixtures thereof. In some cases the reaction can be carried out in the presence of excess amine (III) with no solvents. Suitable bases include, but not limited to, metal alkoxides, tertiary amines and metal hydrides, Method 2

Scheme [2]

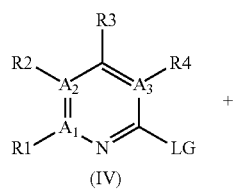

+

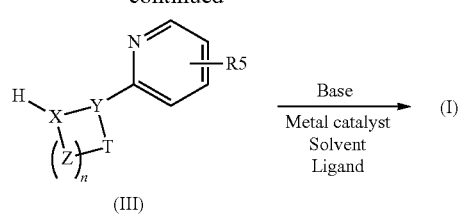

Compounds of the formula (I) can be prepared by treating compounds of the formula (IV), where LG is Cl, Br, I, dialkylborinate, or C1-C4-trialkyl stannane and R1, R2, R3, R4, A1, A2 and A3 are as defined above, and compounds of the formula (III), where X, Y, T, Z, n and R5 are as defined above, in an aprotic or protic solvent in the presence of a stoicheometric or catalytic amount of a base, a metal—(for example, Pd, Cu, Ni) catalyst and a suitable ligands such as trialkyl phosphines or arsines, at a temperature between −20 and 250° C. (heating under conventional or in a microwave reactor) at a pressure between 0-300 psi (Scheme [2]). Suitable solvents include, but are not limited to, water, tetrahydrofuran, 1,4-dioxane, dimethylformamide, dimethylsulfoxide, acetonitrile, chloroform, 1,2-dichloroethane, methylene chloride, and mixtures thereof. Suitable bases include, but not limited to, metal alkoxides, tertiary amines and metal hydrides.

Method 3

Scheme [3]

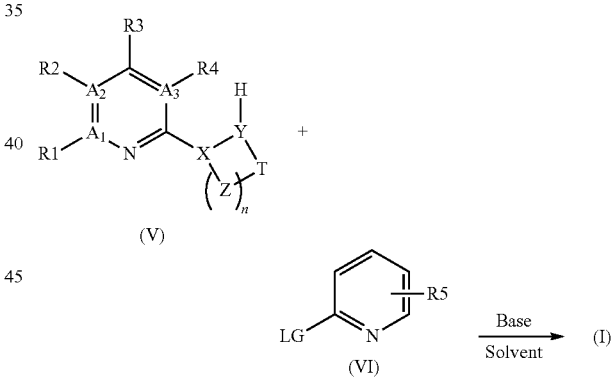

Compounds of the formula (I) can be prepared by treating compounds of the formula (V), where Y=N and R1, R2, R3, R4, X, T, Z, n, A1, A2 and A3 are as defined above, and compounds of the formula (VI), where R5 is as defined above and LG is Cl, Br, I, a sulfone or other leaving group, in an protic or aprotic solvent in the presence of a stoicheometric or catalytic amount of a base at a suitable temperature between −20 and 250° C. (heating conventionally or in a microwave reactor) and at a pressure between 0-300 psi (Scheme [3]). Suitable solvents include, but are not limited to, water, tetrahydrofuran, 1,4-dioxane, dimethylformamide, dimethylsulfoxide, acetonitrile, chloroform, methylene chloride, and mixtures thereof. In some cases the reaction can be carried out in the presence of excess amine (VI) with no solvents. Suitable bases include, but not limited to, metal alkoxides, tertiary amines and metal hydrides, Method 4

Scheme [4]

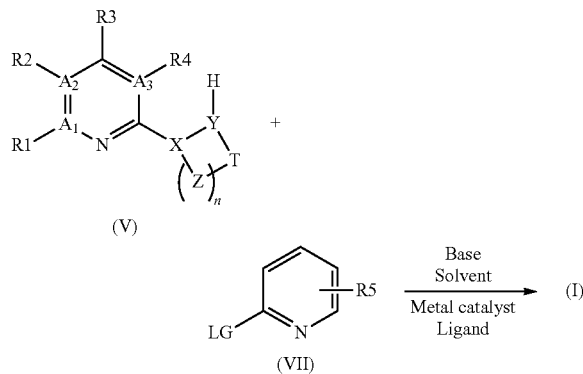

Compounds of the formula (I) can be prepared by treating compounds of the formula (V), where Y=N and R1, R2, R3, R4, X, T, Z, n, A1, A2 and A3 are as defined above and compounds of the formula (VII), where LG is Cl, Br, I, dialkylborinate, or C1-C4-trialkyl stannane and R5 is as defined above, in an aprotic or protic solvent in the presence of a stoicheometric or catalytic amount of a base, a metal— (for example, Pd, Cu, Ni) catalyst and a suitable ligands such as trialkyl phosphines or arsenes, at a temperature between −20 and 250° C. (eating under conventional or in a microwave reactor) at a pressure between 0-300 psi (Scheme [4]). Suitable solvents include, but are not limited to, water, tetrahydrofuran, 1,4-dioxane, dimethylformamide, dimethylsulfoxide, acetonitrile, chloroform, 1,2-dichloroethane, methylene chloride, and mixtures thereof. Suitable bases include, but not limited to, metal alkoxides, tertiary amines and metal hydrides.

Method 5

Scheme [5]

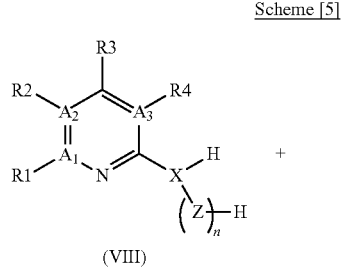

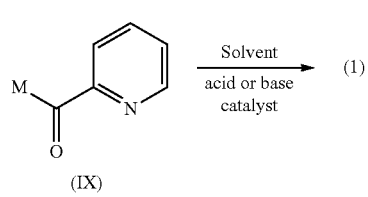

Compounds of the formula (I) can be prepared by treatment of the compounds of the formula (VIII), where R1, R2, R3, R4, X, Z, n, A1, A2, and A3 are as defined above, and compounds of the formula (IX), where M is H or C, in an aprotic solvent in the presence of an acid catalyst under dehydrating conditions such as in a Dean-Stark set-up or additives such as molecular sieves, anhydrous magnesium sulfate (Scheme [5]). Suitable acid catalysts include, but are not limited to, hydrochloric acid, sulfonic acids and sulfuric acid. Preferred solvents include but are not limited to, benzene, toluene, hexanes, pentane, tetrahydrofuran, dialkylethers, 1,4-dioxane, chloroform, methylene chloride, 1,2-dichloroethane, dimethylformamide, and mixtures thereof.

Method 6

Scheme [6]

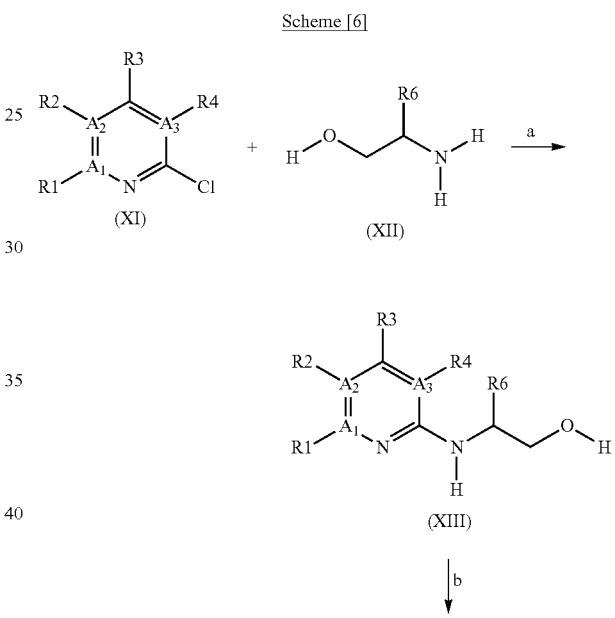

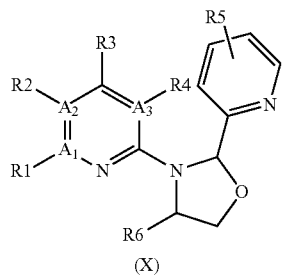

Compounds of the formula (X) can be prepared by a two-step process that includes treatment of compounds of the formula (XI) and compounds of the formula (XII), where R1, R2, R3, R4, R5, A1, A2, and A3 are as defined above, in a sealed tube to selectively displace the chlorine at position 6. Condensation with a pyridine carboxaldehyde under Dean-Stark conditions catalyzed by para-toluenesulfonic acid produces the compound of formula (X).

Method 7

Scheme [7]

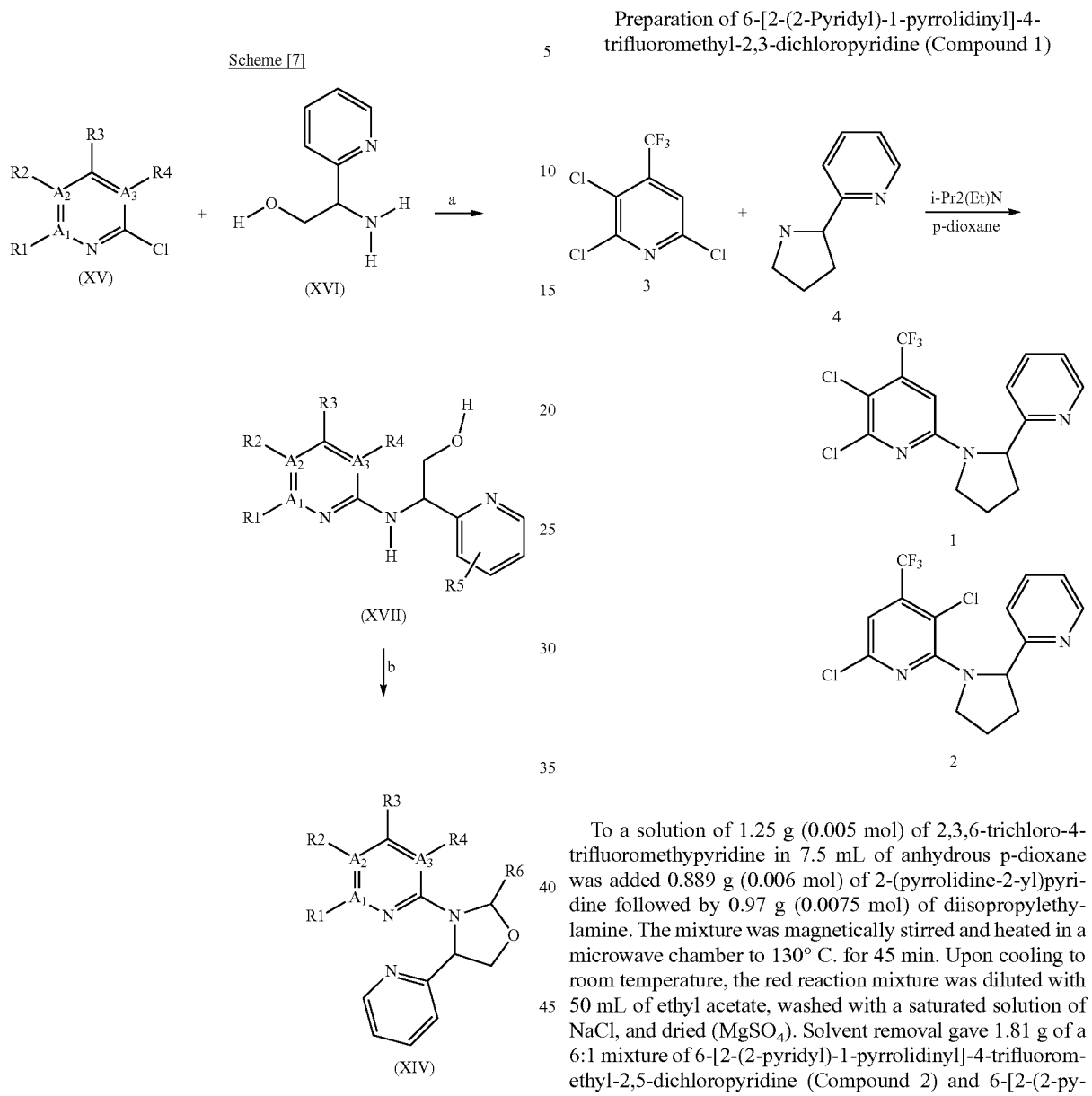

Compounds of the formula (XIV) can be prepared by a two-step process that includes treatment of compounds of the formula (XV) and compounds of the formula (XVI), where R1, R2, R3, R4, A1, A2, and A3 are as defined above, in a sealed tube to selectively displace the chlorine at position 6. Condensation with a carboxaldehyde (R6CHO) under Dean-Stark conditions catalyzed by para-toluenesulfonic acid produces the compound of formula XIV.

EXAMPLES

The examples are for illustration purposes and are not to be construed as limiting the invention disclosed in this document to only the embodiments disclosed in these examples.

Example I

Preparation of 6-[2-(2-Pyridyl)-1-pyrrolidinyl]-4-trifluoromethyl-2,3-dichloropyridine (Compound 1)

To a solution of 1.25 g (0.005 mol) of 2,3,6-trichloro-4-trifluoromethypyridine in 7.5 mL of anhydrous p-dioxane was added 0.889 g (0.006 mol) of 2-(pyrrolidine-2-yl)pyridine followed by 0.97 g (0.0075 mol) of diisopropylethylamine. The mixture was magnetically stirred and heated in a microwave chamber to 130° C. for 45 min. Upon cooling to room temperature, the red reaction mixture was diluted with 50 mL of ethyl acetate, washed with a saturated solution of NaCl, and dried (MgSO$_4$). Solvent removal gave 1.81 g of a 6:1 mixture of 6-[2-(2-pyridyl)-1-pyrrolidinyl]-4-trifluoromethyl-2,5-dichloropyridine (Compound 2) and 6-[2-(2-pyridyl)-1-pyrrolidinyl]-4-trifluoromethyl-2,3-dichloropyridine (Compound 1). Column chromatography on silica gel eluting with 20% ethyl acetate/hexane gave 1.05 g of 98% pure Compound 2 and 0.41 g of 1:1 mixture of Compound 2:Compound 1. This mixture was further separated as above to give 0.18 g of Compound 2 and 0.15 g of Compound 1.

Compound 1: $^1$H NMR (300 MHz, CDCl$_3$) δ 8.58 (dd, J=4.8, 1.0 Hz, 1H), 7.61 (dt, J=2.0, 7.9 Hz, 1H), 7.17 (ddd, J=4.8, 2.0, 1.0H), 7.11 (d, J=7.9 Hz, 1H), 6.40 (brs, 1H), 5.04 (brs, 1H), 3.83 (m, 1H), 3.65 (m, 1H), 2.43 (m, 1H), 2.1 (m, 3H). Exact mass for C$_{15}$H$_{12}$C$_2$F$_3$N$_3$. Calcd, 316.0355. Found, 361.0358.

Compound 2: $^1$H NMR (300 MHz, CDCl$_3$) δ 8.54 (dq, J=4.8, 1.0 Hz, 1H), 7.56 (dt, J=2.0, 7.9 Hz, 1H), 7.24 (d, J=7.9 Hz, 1H), 7.16 (ddd, J=4.8, 2.0, 1.0, 1H), 6.84 (brs, 1H), 5.50 (t, J=6.7 Hz, 1H), 4.22 (m, 1H), 3.81 (m, 1H), 2.43 (m, 1H), 2.1 (m, 3H). Exact mass for C$_{15}$H$_{12}$Cl$_2$F$_3$N$_3$. Calcd, 316.0355; Found, 361.0357.

Example II

Preparation of 2-(2-Pyridyl)piperidin-2-yl)-4-trifluoromethyl-5,6-dichloropyridine (Compound 6) and 2-(2-Pyridyl)piperidin-2-yl)-4-trifluoromethyl-3,6-dichloropyridine (Compound 7)

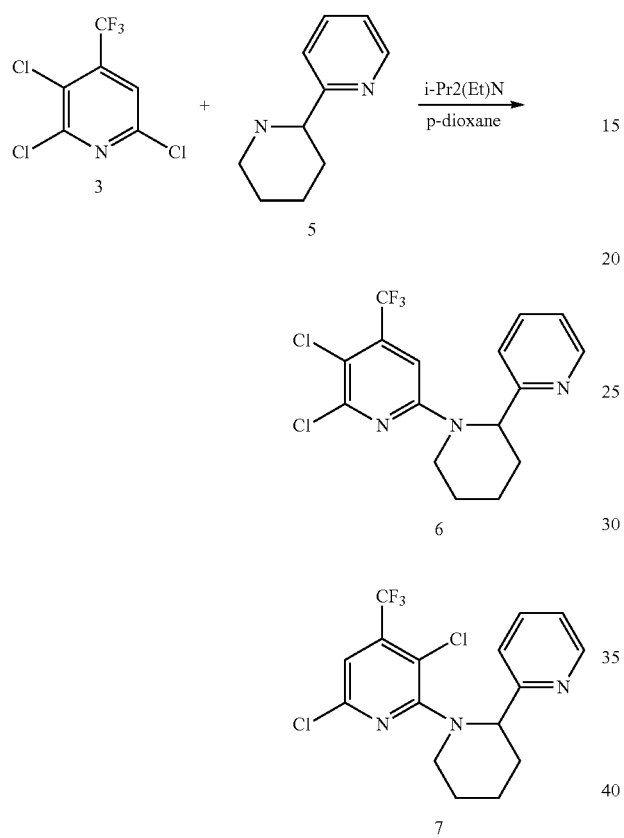

To a solution of 1.25 g (0.005 mol) of 2,3,6-trichloro-4-trifluoromethypyridine in 7.5 mL of anhydrous p-dioxane was added 0.973 g (0.006 mol) of 2-(piperidin-2-yl)pyridine followed by 0.97 g (0.0075 mol) of diisopropylethylamine. The mixture was magnetically stirred and heated in a microwave chamber to 130° C. for 45 min. Upon cooling to room temperature, the red reaction mixture was diluted with 50 mL of ethyl acetate, washed with a saturated solution of NaCl, and dried (MgSO$_4$). Solvent removal gave 2.0 g of a 3:2 mixture of 2-(2-pyridyl)piperidin-2-yl)-4-trifluoromethyl-5,6-dichloropyridine (Compound 6) and 2-(2-pyridyl)piperidin-2-yl)-4-trifluoromethyl-3,6-dichloropyridine (Compound 7). A 0.20 g sample was purified on silica gel eluting with 10% ethyl acetate/hexane to give 0.14 g of 1:1 mixture of Compound 6:Compound 7, which could not be further purified.

Compound 6: $^1$H NMR (300 MHz, CDCl$_3$) δ 8.58 (m, 1H), 7.60 (m, 1H), 7.0 (m, 2H), 6.75 (brs, 1H), 5.04 (brs, 1H), 3.3 (m, 2H), 2.6 (m, 1H), 1.5-2.2 (m, 5H).

Compound 7: $^1$H NMR (300 MHz, CDCl$_3$) δ 8.54 (m, 1H), 7.56 m, 1H), 7.3 (m, 1H), 7.1 (m, 2H), 7.05 (brs, 1H), 5.60 (m, 1H), 4.20 (m, 1H), 3.5 (m, 1H), 2.60 (m, 1H), 1.5-2.1 (m, 4H).

Example III

Preparation of 2,6-Dichloro-4-trifluoromethyl-3-trimethylsilanylpyridine (Compound 8)

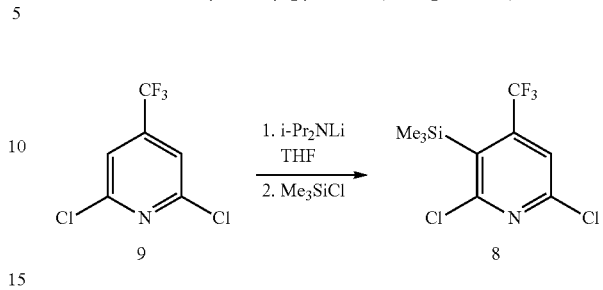

A dry 100 mL 3 neck rb flask was charged with diisopropylamine (2.15 mL, 15.3 mmol) and 40 mL of anhydrous THF. Reaction mixture was cooled at −20° C. under N$_2$. A 2.5 M solution of n-BuLi in Hexane (5.90 mL, 14.8 mmol) was added dropwise via a syringe. The resulting reaction mixture was then cooled at −78° C. A solution of 2,6-dichloro-4-trifluoromethylpyridine (3.0 g, 14 mmol) in 5 mL of anhydrous THF was added slowly via an addition funnel to give a pale yellow solution. Reaction mixture stirred at −78° C. for 2 h. After which time, a solution of TMSCl (2.0 mL, 15.8 mmol) in 5 mL of THF was added dropwise via an addition funnel. The resulting reaction mixture was allowed to slowly warm up to room temperature and stirred over night. Reaction mixture was added to 150 mL of Et$_2$O, washed with dilute HCl, then washed with aq. NaHCO$_3$, dried over MgSO$_4$, filtered and concentrated to give 3.80 g (95%) of 2,6-dichloro-4-trifluoromethyl-3-trimethylsilanylpyridine (Compound 8) as a brown oil:

$^1$H NMR (300 MHz, CDCl$_3$) δ 0.5 (s, 9H), 7.55 (s, 1H).

Example IV

Preparation of 2-(2-Pyridyl)pyrrolidine-2-yl)-4-trifluoromethyl-5-trimethylsilanylpyridine-6-chloropyridine (Compound 10)

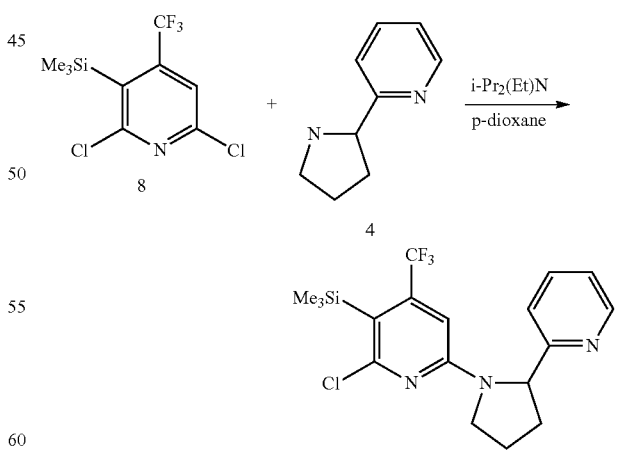

To a solution of 1.44 g (0.005 mol) of 2,6-dichloro-4-trifluoromethyl-3-trimethylsilanylpyridine (Compound 8) in 7.5 mL of anhydrous p-dioxane was added 0.889 g (0.006 mol) of 2-(pyrrolidine-2-yl)pyridine followed by 0.97 g (0.0075 mol) of diisopropylethylamine. The mixture was magnetically stirred and heated in a microwave chamber to 150° C. for 1 hr. Upon cooling to room temperature, the red reaction mixture was diluted with 50 mL of ethyl ether, washed with a saturated solution of NaCl, and dried ($MgSO_4$). Solvent removal gave 2.05 g of an orange oil. Column chromatography on silica gel eluting with 10% ethyl acetate/hexane gave 0.95 g (48% yield) of 2-(2-pyridyl)pyrrolidine-2-yl)-4-trifluoromethyl-5-trimethylsilanylpyridine-6-chloropyridine (Compound 10).

$^1$H NMR (300 MHz, $CDCl_3$) δ 8.58 (dd, J=4.8, 1.0 Hz, 1H), 7.62 (dt, J=2.0, 7.5 Hz, 1H), 7.15 (m, 2H), 6.45 (brs, 1H), 5.04 (brs, 1H), 3.8 (m, 1H), 3.72 (m, 1H), 2.45 (m, 1H), 2.05-2.22 (m, 3H), 0.4 (s, 9H). Exact mass for $C_{15}H_{21}ClF_3N_3Si$. Calcd, 399.1140. Found, 399.1146.

Example V

Preparation of 2-(2-Pyridyl)pyrrolidino-2-yl)-4-trifluoromethyl-5-trimethylsilanylpyridinepyridine (Compound 11)

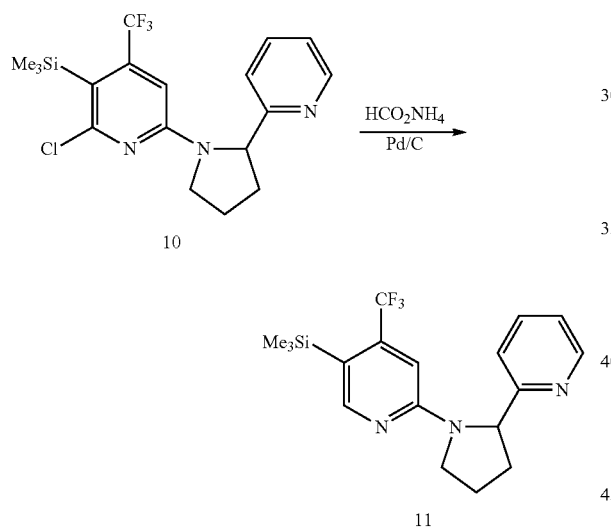

To a solution of 0.24 g (0.6 mmol) 2-(2-pyridyl)pyrrolidino-2-yl)-4-trifluoromethyl-5-trimethylsilanylpyridine-6-chloropyridine (Compound 10) in 5 mL of methanol was added 0.252 g (4 mmol) of ammonium formate followed by 0.1 g of 5% Pd on carbon. The mixture was magnetically stirred and heated in a microwave chamber to 100° C. for 1.5 hr. Upon cooling to room temperature, the reaction mixture was filtered through a plug of Celite and solvent was removed. The residue was dissolved in methylene chloride washed with a saturated solution of NaCl and dried ($MgSO_4$). Solvent removal gave 0.185 g (84% yield) of a 95% pure 2-(2-pyridyl)pyrrolidine-2-yl)-4-trifluoromethyl-5-trimethylsilanylpyridinepyridine (Compound 11).

$^1$H NMR (300 MHz, $CDCl_3$) δ 8.58 (dd, J=4.8, 1.0 Hz, 1H), 8.37 (s, 1H), 7.62 (dt, J=2.0, 7.5 Hz, 1H), 7.15 (m, 2H), 6.55 (brs, 1H), 5.20 (brs, 1H), 3.91 (m, 1H), 3.70 (m, 1H), 2.45 (m, 1H), 2.22 (m, 1H), 2.10 (m 2H), 0.4 (s, 9H). Exact mass for $C_{11}H_{22}IF_3N_3Si$. Calcd, 365.1535. Found, 399.1532.

Example VI

Synthesis of 2-chloro-6-[4-isopropyl-2-(2-pyridyl)oxazolidin-3-yl]-4-(trifluoromethyl)pyridine-3-carbonitrile (Compound 12)

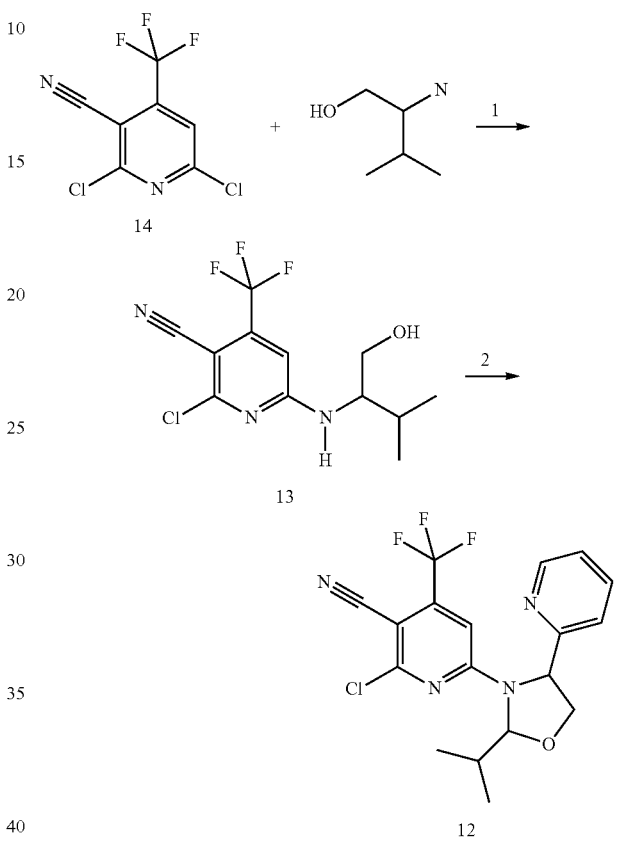

Step 1: Preparation of 2-chloro-6-[[1-(hydroxymethyl)-2-methyl-propyl]amino]-4-(trifluoromethyl)pyridine-3-carbonitrile intermediate Neat 3-cyano-2,6-dichloro-4-trifluoromethylpyridine (0.641 g, 6 mmol) (Compound 14) was added by pipette at a dropwise rate over 3 minutes to 2-amino-3-methyl-butan-1-ol (1.5 g, 6 mmol) (Compound 15). Di-isopropylamine (0.9 g, 7 mmol) was added after 10 minutes and the resultant mixture was heated in a sealed tube at 70° C. for 30 minutes to selectively displace the chlorine at position 6 before quenching in ice-cold water and extracted with dichloromethane. Organic extracts were washed twice with water, dried over sodium sulfate and concentrated under reduced pressure. The residue was washed with diethylether and the resultant solid was used in the next step without further purification. 2-Chloro-6-[[1-(hydroxymethyl)-2-methyl-propyl]amino]-4-(trifluoromethyl)pyridine-3-carbonitrile (Compound 13) was isolated in 50% yield.

$^1$HNMR ($CDCl_3$, 400 MHz) δ/ppm 6.66 (s, 1H), 5.63 (br, 1H), 4.09 (br, 0.7H), 3.81 (t, J=4.5 Hz, 2.4H), 2.01 (octet, J=6.9 Hz, 1H), 1.70 (br t, J=4.9 Hz, 0.9H), 1.03 (d, J=6.7 Hz, 3H), 1.00 (d, J=6.8 Hz, 3H).

Step 2: Synthesis of 2-chloro-6-[4-isopropyl-2-(2-pyridyl)oxazolidin-3-yl]-4-(trifluoromethyl)pyridine-3-carbonitrile Pyridine-2-carboxaldehyde (207 mg, 1.9 mmol) was added to a toluene solution (15 mL) of 2-chloro-6-[[1-(hydroxymethyl)-2-methyl-propyl]amino]-4-(trifluoromethyl)pyridine-3-carbonitrile (400 mg, 1.3 mmol) (Compound 13) followed by a catalytic amount of para-toluene sulfonic acid (50 mg). The reactants were refluxed for 6 hours in a Dean-Stark apparatus, concentrated under reduced pressure, adsorbed onto silica and purified using a neutral alumina column, eluting with a mobile phase of 10% ethyl acetate in hexane. 2-Chloro-6-[4-isopropyl-2-(2-pyridyl)oxazolidin-3-yl]-4-(trifluoromethyl)pyridine-3-carbonitrile (Compound 12) was isolated as a solid in 20% yield. mp 112-115° C.

$^1$HNMR (CDCl$_3$, 400 MHz) δ/ppm 8.49 (br, 0.7H), 7.73 (dt, J$^1$=6.7 Hz, J$^2$=1.8 Hz, 0.8H), 7.42 (br, 0.8H), 7.26 (br), 6.61 (br, 0.4H), 6.38 (br, 0.9H), 4.52 (br, 1.5H), 4.21 (d, J=8.4 Hz, 1.3H), 2.42 (br, 0.8H), 1.06 (d, J=6.6 Hz, 3H), 0.97 (d, J=6.6 Hz, 3-1); ES/MS 397.0 (M$^+$).

Example VII

Synthesis of 2-chloro-6-[4-methyl-2-(2-pyridyl)oxazolidin-3-yl]-4-(trifluoromethyl)pyridine-3-carbonitrile (Compound 16)

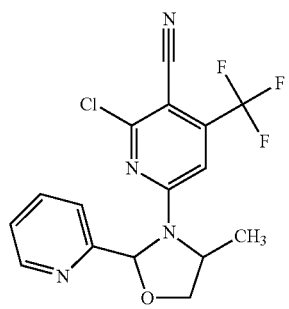

16

Step 1: Synthesis of 2-chloro-6-[[1-(hydroxymethyl)-2-methyl]amino]-4-(trifluoromethyl)pyridine-3-carbonitrile Neat 3-cyano-2,6-dichloro-4-trifluoromethylpyridine (0.641 g, 6 mmol) was added by pipette at a dropwise rate over 3 minutes to 2-aminopropanol (1.5 g, 6 mmol). Di-isopropylamine (0.9 g, 7 mmol) was added after 10 minutes and the resultant mixture was heated in a sealed tube at 70° C. for 30 minutes to selectively displace the chlorine at position 6 before quenching in ice-cold water and extracted with dichloromethane. Organic extracts were washed twice with water, dried over sodium sulfate and concentrated under reduced pressure. The residue was washed with diethylether and the resultant solid was used in the next step without further purification. 2-Chloro-6-[[1-(hydroxymethyl)-2-methyl]amino]-4-(trifluoromethyl)pyridine-3-carbonitrile was isolated in 52% yield.

$^1$HNMR (CDCl$_3$, 400 MHz) δ/ppm 6.63 (s, 1H), 4.27 (br, 0.8H), 3.84-3.79 (m, 1.2H), 3.70-3.65 (m, 1.3H), 1.80 (br t, 0.8H), 1.58 (s, 1.3H), 1.30 (d, J=6.7 Hz, 3H).

Step 2: Synthesis of 2-chloro-6-[4-methyl-2-(2-pyridyl)oxazolidin-3-yl]-4-(trifluoromethyl)pyridine-3-carbonitrile Pyridine-2-carboxaldehyde (207 mg, 1.9 mmol) was added to a toluene solution (15 mL) of 2-chloro-6-[[1-(hydroxymethyl)-2-methyl]amino]-4-(trifluoromethyl)pyridine-3-carbonitrile (400 mg, 1.3 mmol) followed by a catalytic amount of para-toluene sulfonic acid (50 mg). The reactants were refluxed for 6 hours in a Dean-Stark apparatus, concentrated under reduced pressure, adsorbed onto silica and purified using a neutral alumina column, eluting with a mobile phase of 10% ethyl acetate in hexane. 2-Chloro-6-[4-methyl-2-(2-pyridyl)oxazolidin-3-yl]-4-(trifluoromethyl)pyridine-3-carbonitrile (Compound 16) was isolated as a solid in 55% yield. mp 90-93° C.

$^1$HNMR (CDCl$_3$, 400 MHz) S/ppm 8.63 (d, J=4.8 Hz, 0.2H), 8.52 (br, 0.6H), 7.78-7.73 (m, 1H), 7.54 (d, J=7.9 Hz, 0.2H), 7.43 (br, 0.8H), 7.34-7.26 (m), 6.85 (br, 0.2H), 6.67 (m, 0.5H), 6.42-6.17 (br, 1.4H), 4.71-4.43 (br, 2H), 4.29 (t, 0.3H), 4.11-4.10 (m, 0.2H), 3.98 (d, J=8.2 Hz, 1H), 1.49 (d, J=6.3 Hz, 3H); ES/MS 369.0 (M$^+$).

Example VIII

Synthesis of 2-chloro-6-[5-ethyl-2-(2-pyridyl)oxazolidin-3-yl]-4-(trifluoromethyl)pyridine-3-carbonitrile (Compound 17)

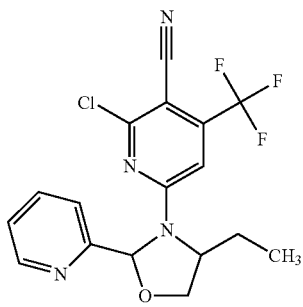

17

Step 1: Synthesis of 2-chloro-6-(2-hydroxybutylamino)-4-(trifluoromethyl)pyridine-3-carbonitrile Neat 3-cyano-2,6-dichloro-4-trifluoromethylpyridine (0.641 g, 6 mmol) was added by pipette at a dropwise rate over 3 minutes to 2-aminobutanol (1.5 g, 6 mmol). Di-isopropylamine (0.9 g, 7 mmol) was added after 10 minutes and the resultant mixture was heated in a sealed tube at 70° C. for 30 minutes to selectively displace the chlorine at position 6 before quenching in ice-cold water and extracted with dichloromethane. Organic extracts were washed twice with water, dried over sodium sulfate and concentrated under reduced pressure. The residue was washed with diethylether and the resultant solid was used in the next step without further purification. 2-Chloro-6-(2-hydroxybutylamino)-4-(trifluoromethyl)pyridine-3-carbonitrile was isolated in 55% yield.

$^1$HNMR (CDCl$_3$, 400 MHz) δ/ppm 6.64 (s, 1H), 5.96 (br, 1H), 3.78 (br, 1H), 3.32 (br, 1H), 1.94 (br d, J=4.1 Hz, 1H), 1.65-1.50 (m, 4H), 1.02 (t, J=7.5 Hz, 3H).

Step 2: Synthesis of 2-chloro-6-[5-ethyl-2-(2-pyridyl)oxazolidin-3-yl]-4-(trifluoromethyl)pyridine-3-carbonitrile Pyridine-2-carboxaldehyde (207 mg, 1.9 mmol) was added to a toluene solution (15 mL) of 2-chloro-6-(2-hydroxybutylamino)-4-(trifluoromethyl)pyridine-3-carbonitrile (400 mg, 1.3 mmol) followed by a catalytic amount of para-toluene sulfonic acid (50 mg). The reactants were refluxed for 6 hours in a Dean-Stark apparatus, concentrated under reduced pressure, adsorbed onto silica and purified using a neutral alumina column, eluting with a mobile phase of 10% ethyl acetate in hexane. 2-Chloro-6-[5-ethyl-2-(2-pyridyl)oxazolidin-3-yl]-4-(trifluoromethyl)pyridine-3-carbonitrile (Compound 17) was isolated as a solid in 37% yield. mp 115-118° C.

$^1$HNMR (CDCl$_3$, 400 MHz) δ/ppm 8.59 (d, J=4.5 Hz, 0.7H), 7.76 (t, J=7.5 Hz, 0.8; H), 7.46 (dd, J$^1$=7.8 Hz, J$^2$=1.0 Hz, 0.8H), 7.31 (br, 0.7H), 6.84 (br, 0.6H), 6.66 (br, 0.2H), 6.12 (br, 0.7H), 4.75 (br, 0.1H), 4.44 (br, 0.6H), 4.24 (br, 0.9H), 4.03 (t, J=9.6 Hz, 0.3H), 3.53 (br, 1H), 1.97-1.80 (m, 2.1H), 1.10-1.02 (m, 3H); ES/MS 383.0 (M$^+$).

Example IX

2-chloro-6-[4-phenyl-2-(2-pyridyl)oxazolidin-3-yl]-4-(trifluoromethyl)pyridine-3-carbonitrile (Compound 18)

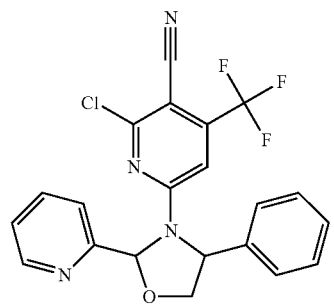 [SMILES: N#Cc1c(C(F)(F)F)cc(N2C(c3ccccc3)COC2c2ccccn2)nc1Cl]

18

Step 1: Synthesis of 2-chloro-6-[[1-(hydroxymethyl)-2-phenyl]amino]-4-(trifluoromethyl)pyridine-3-carbonitrile Neat 3-cyano-2,6-dichloro-4-trifluoromethylpyridine (0.641 g, 6 mmol) was added by pipette at a dropwise rate over 3 minutes to 2-amino-2-phenylethanol (1.5 g, 6 mmol). Di-isopropylamine (0.9 g, 7 mmol) was added after 10 minutes and the resultant mixture was heated in a sealed tube at 70° C. for 30 minutes to selectively displace the chlorine at position 6 before quenching in ice-cold water and extracted with dichloromethane. Organic extracts were washed twice with water, dried over sodium sulfate and concentrated under reduced pressure. The residue was washed with diethylether and the resultant solid was used in the next step without further purification. 2-Chloro-6-[[1-(hydroxymethyl)-2-phenyl]amino]-4-(trifluoromethyl)pyridine-3-carbonitrile was isolated in 60% yield.

$^1$HNMR (CDCl$_3$, 400 MHz) δ/ppm 7.42-7.33 (m, 5H), 6.51 (br, 2H), 4.06-4.03 (m, 1.4H), 3.96 (br, 1.1H), 1.89 (br, 0.96H), 1.60 (m, 1.1H).

Step 2: Synthesis of 2-chloro-6-[4-phenyl-2-(2-pyridyl)oxazolidin-3-yl]-4-(trifluoromethyl)pyridine-3-carbonitrile Pyridine-2-carboxaldehyde (207 mg, 1.9 mmol) was added to a toluene solution (15 mL) of 2-chloro-6-[[1-(hydroxymethyl)-2-phenyl]amino]-4-(trifluoromethyl)pyridine-3-carbonitrile (400 mg, 1.3 mmol) followed by a catalytic amount of para-toluene sulfonic acid (50 mg). The reactants were refluxed for 6 hours in a Dean-Stark apparatus, concentrated under reduced pressure, adsorbed onto silica and purified using a neutral alumina column, eluting with a mobile phase of 10% ethyl acetate in hexane. 2-Chloro-6-[4-phenyl-2-(2-pyridyl)oxazolidin-3-yl]-4-(trifluoromethyl)pyridine-3-carbonitrile (Compound 18) was isolated as a solid in 19% yield. mp 198-200° C.

$^1$HNMR (CDCl$_3$, 400 MHz) δ/ppm 8.53 (br, 0.8H), 7.79 (dt, J$^1$=7.6 Hz, J$^2$=1.4 Hz, 1H), 7.57 (br, 1.1H), 7.42-7.37 (m, 7.2H), 7.29 (br), 6.78 (br, 0.9H), 6.43 (br, 1.2H), 5.60 (br, 0.2H), 5.23 (br, 1H), 5.00 (br, 1.1H), 4.17-4.13 (m, 1.4H); ES/MS 431.0 (M$^+$).

Example X

2-Chloro-6-[5-ethyl-2-(2-pyridyl)oxazolidin-3-yl]-4-(trifluoromethyl)pyridine-3-carbonitrile (Compound 19)

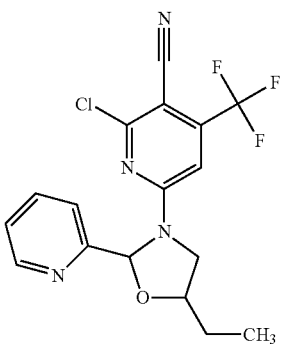 [SMILES: CCC1CN(c2cc(C(F)(F)F)c(C#N)c(Cl)n2)C(c2ccccn2)O1]

19

Step 1: Synthesis of 2-chloro-6-(2-hydroxybutylamino)-4-(trifluoromethyl)pyridine-3-carbonitrile Neat 3-cyano-2,6-dichloro-4-trifluoromethylpyridine (0.641 g, 6 mmol) was added by pipette at a dropwise rate over 3 minutes to 1-aminopropane-2-ol (1.5 g, 6 mmol). Di-isopropylamine (0.9 g, 7 mmol) was added after 10 minutes and the resultant mixture was heated in a sealed tube at 70° C. for 30 minutes to selectively displace the chlorine at position 6 before quenching in ice-cold water and extracted with dichloromethane. Organic extracts were washed twice with water, dried over sodium sulfate and concentrated under reduced pressure. The residue was washed with diethylether and the resultant solid was used in the next step without further purification.

2-chloro-6-(2-hydroxybutylamino)-4-(trifluoromethyl)pyridine-3-carbonitrile was isolated in 55% yield.

$^1$HNMR (CDCl$_3$, 400 MHz) δ/ppm 6.64 (s, 1H), 5.63 (br, 1H), 4.21 (br, 0.7H), 3.83-3.73 (m, 2.5H), 2.18 (d, J=0.8 Z, 2H), 1.76-1.61 (m, 3.2H), 1.54-1.51 (m, 0.6H), 1.44 (d, J=6.7 Hz, 0.3H), 1.00 (t, J=7.4 Hz, 3H).

Step 2: Synthesis of 2-chloro-6-[5-ethyl-2-(2-pyridyl)oxazolidin-3-yl]-4-(trifluoromethyl)pyridine-3-carbonitrile Pyridine-2-carboxaldehyde (207 mg, 1.9 mmol) was added to a toluene solution (15 mL) of 2-chloro-6-(2-hydroxybutylamino)-4-(trifluoromethyl)pyridine-3-carbonitrile (400 mg, 1.3 mmol) followed by a catalytic amount of para-toluene sulfonic acid (50 mg). The reactants were refluxed for 6 hours in a Dean-Stark apparatus, concentrated under reduced pressure, adsorbed onto silica and purified using a neutral alumina column, eluting with a mobile phase of 10% ethyl acetate in hexane. 2-Chloro-6-[5-ethyl-2-(2-pyridyl)oxazolidin-3-yl]-4-(trifluoromethyl)pyridine-3-carbonitrile (Compound 19) was isolated as a solid in 46% yield. mp 99-102° C.

$^1$HNMR (CDCl$_3$, 400 MHz) δ/ppm 8.62-8.63 (m, 0.4H), 8.51 (br, 0.2H), 7.79-7.74 (m, 0.8H), 7.54 (d, J=7.9 Hz, 0.5H), 7.42 (br, 0.3H), 7.34-7.31 (m, 0.5H), 6.92 (br, 0.5H), 6.64 (br, 0.2H), 6.40 (br, 0.4H), 6.12 (br, 0.5H), 4.66 (br, 0.4H), 4.38 (br, 0.6H), 4.21-4.20 (m, 1.4H), 4.11 (d, J=8.6 Hz, 0.5H); 2.09-1.98 (m 0.8H), 1.87-1.78 (m, 1.3H), 1.05-1.00 (m, 3H); ES/MS 383.0 (M$^+$).

Example XI

Insecticidal Testing

Insecticidal Test for Green Peach Aphid (*Myzus persicae*) in Foliar Spray Assay Cabbage seedlings grown in 3-inch pots, with 2-3 small (3-5 cm) true leaves, were used as test substrate. The seedlings were infested with 20-50 green peach aphids (wingless adult and nymph) 1-2 days prior to chemical application. Four seedlings were used for each treatment. Selected compounds (2 mg), many of which are described above, were dissolved in 2 ml of acetone:methanol (1:1) solvent, forming stock solutions of 1000 ppm. The stock solutions were diluted 5× with 0.025% Tween 20 in H$_2$O to obtain a solution at 200 ppm. A hand-held Devilbiss aspirator sprayer was used for spraying a solution to both sides of cabbage leaves until runoff. Reference plants (solvent check) were sprayed with the diluent only. Treated plants were held in a holding room for three days at approximately 23° C. and 40% relative humidity prior to grading. Evaluation was conducted by counting the number of live aphids per plant under a microscope.

Insecticidal activity was measured by using Abbott's correction formula:

$$\text{Corrected \% Control} = 100 \times (X-Y)/X$$

where
  X=No. of live aphids on solvent check plants
  Y=No. of live aphids on treated plants The results of this test are set forth in the column labelled "Green Peach Aphid" in Table 1 below, in which letter designations represent ranges of percent control as follows:
  A=80-100% control
  B=60-79% control
  C=40-59% control
  D=20-39% control
  E=0-19% control Insecticidal Test for Beet Armyworm (*Spodoptera exigua*).

To prepare test solution, the test compound was formulated at 2000 ppm solution in 2 mL of 9 acetone: 1 tap water. 50 μL of the test solution (50 g/cm$^2$ dose for each well) was pipetted upon the surface of 1 mL of lepidopteran diet (Southland Multi-Species Lepidopteran Diet) contained in each of eight wells per insect species (one well=1 replication). A second-instar beet armyworm was placed upon the treated diet in each well (one insect per well) once the solvent had air-dried. Trays containing the treated diet and larvae were covered and then held in a growth chamber at 25° C., 50-55% RH, and 16 hr light:8 hr dark for 5 days. Observation were conducted 2 and 5 days after treatment and infestation to score the number of dead insects per 8-well treatment.

The results of this test are set forth in the column labelled "Beet Armyworm" in Table 1 below, in which letter designations represent ranges of percent control as set forth above.

TABLE 1

| Compound No. | STRUCTURE | Beet Army-worm | Green Peach Aphid |
|---|---|---|---|
| 1 | (structure) | B | A |
| 2 | (structure) | B | C |
| 3 | (structure) | D | D |
| 6 | (structure) | A | D |

TABLE 1-continued

| Compound No. | STRUCTURE | Beet Army-worm | Green Peach Aphid |
|---|---|---|---|
| 10 | [structure: 6-chloro-5-(trimethylsilyl)-4-(trifluoromethyl)-2-(2-(pyridin-2-yl)pyrrolidin-1-yl)pyridine] | E | E |
| | [structure: 5-bromo-6-chloro-4-(trifluoromethyl)-2-(2-(pyridin-2-yl)pyrrolidin-1-yl)pyridine] | E | D |
| 11 | [structure: 5-tert-butyl-4-(trifluoromethyl)-2-(2-(pyridin-2-yl)pyrrolidin-1-yl)pyridine] | A | A |
| | [structure: 5-chloro-4-(trifluoromethyl)-2-(2-(pyridin-2-yl)pyrrolidin-1-yl)pyridine] | D | E |
| | [structure: 3,5-dichloro-4-(trifluoromethyl)-2-(2-(pyridin-2-yl)pyrrolidin-1-yl)pyridine] | B | E |
| 16 | [structure: 2-chloro-6-(4-methyl-2-(pyridin-2-yl)oxazolidin-3-yl)-4-(trifluoromethyl)nicotinonitrile] | E | E |
| 17 | [structure: 2-chloro-6-(4-ethyl-2-(pyridin-2-yl)oxazolidin-3-yl)-4-(trifluoromethyl)nicotinonitrile] | E | E |
| 12 | [structure: 2-chloro-6-(4-isopropyl-2-(pyridin-2-yl)oxazolidin-3-yl)-4-(trifluoromethyl)nicotinonitrile] | E | D |
| 18 | [structure: 2-chloro-6-(4-phenyl-2-(pyridin-2-yl)oxazolidin-3-yl)-4-(trifluoromethyl)nicotinonitrile] | E | E |
| 19 | [structure: 2-chloro-6-(5-methyl-2-(pyridin-2-yl)oxazolidin-3-yl)-4-(trifluoromethyl)nicotinonitrile] | C | C |

ACID & SALT DERIVATIVES, AND SOLVATES

The compounds of Formula I can be in the form of pesticidally acceptable acid addition salts.

By way of non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic, acids.

Additionally, by way of non-limiting example, an acid function can form salts including those derived from alkali or alkaline earth metals and those derived from ammonia and amines. Examples of preferred cations include sodium, potassium, magnesium, and aminium cations.

The salts are prepared by contacting the free base form with a sufficient amount of the desired acid to produce a salt. The free base forms may be regenerated by treating the salt with a suitable dilute aqueous base solution such as dilute aqueous NaOH, potassium carbonate, ammonia, and sodium bicarbonate.

As an example, in many cases, a pesticide is modified to a more water soluble form e.g. 2,4-dichlorophenoxy acetic acid dimethyl amine salt is a more water soluble form of 2,4-dichlorophenoxy acetic acid a well known herbicide.

The compounds disclosed in this application can also form stable complexes with solvent molecules that remain intact after the non-complexed solvent molecules are removed from the compounds. These complexes are often referred to as "solvates".

STEREOISOMERS

Certain compounds disclosed in this application can exist as one or more stereoisomers. The various stereoisomers include geometric isomers, diastereomers, and enantiomers. Thus, the compounds disclosed in this application include racemic mixtures, individual stereoisomers, and optically active mixtures.

It will be appreciated by those skilled in the art that one stereoisomer may be more active than the others. Individual stereoisomers and optically active mixtures may be obtained by selective synthetic procedures, by conventional synthetic procedures using resolved starting materials, or by conventional resolution procedures.

PESTS

In another embodiment, the invention disclosed in this document can be used to control pests.

In another embodiment, the invention disclosed in this document can be used to control pests of the Phylum Nematoda.

In another embodiment, the invention disclosed in this document can be used to control pests of the Phylum Arthropoda.

In another embodiment, the invention disclosed in this document can be used to control pests of the Subphylum Chelicerata.

In another embodiment, the invention disclosed in this document can be used to control pests of the Class Arachnida.

In another embodiment, the invention disclosed in this document can be used to control pests of the Subphylum Myriapoda.

In another embodiment, the invention disclosed in this document can be used to control pests of the Class Symphyla.

In another embodiment, the invention disclosed in this document can be used to control pests of the Subphylum Hexapoda.

In another embodiment, the invention disclosed in this document can be used to control pests of the Class Insecta.

In another embodiment, the invention disclosed in this document can be used to control Coleoptera (beetles). A non-exhaustive list of these pests includes, but is not limited to, *Acanthoscelides* spp. (weevils), *Acanthoscelides obtectus* (common bean weevil), *Agrilus planipennis* (emerald ash borer), *Agriotes* spp. (wireworms), *Anoplophora glabripennis* (Asian longhorned beetle), *Anthonomus* spp. (weevils), *Anthonomus grandis* (boll weevil), *Aphidius* spp., *Apion* spp. (weevils), *Apogonia* spp. (grubs), *Ataenius sprelulus* (Black Turgrass Ataenius), *Atomaria linearis* (pygmy mangold beetle), *Aulacophore* spp., *Bothynoderes punctiventris* (beet root weevil), *Bruchus* spp. (weevils), *Bruchus pisorum* (pea weevil), *Cacoesia* spp., *Callosobruchus maculatus* (southern cow pea weevil), *Carpophilus hemipteras* (dried fruit beetle), *Cassida vittata, Cerosterna* spp., *Cerotoma* spp. (chrysomeids), *Cerotoma trifurcata* (bean leaf beetle), *Ceutorhynchus* spp. (weevils), *Ceutorhynchus assimilis* (cabbage seedpod weevil), *Ceutorhynchus napi* (cabbage curculio), *Chaetocnema* spp. (chrysomelids), *Colaspis* spp. (soil beetles), *Conoderus scalaris, Conoderus stigmosus, Conotrachelus nenuphar* (plum curculio), *Cotinus nitidis* (Green June beetle), *Crioceris asparagi* (asparagus beetle), *Cryptolestes ferrugineus* (rusty grain beetle), *Cryptolestes pusillus* (flat grain beetle), *Cryptolestes turcicus* (Turkish grain beetle), *Ctenicera* spp. (wireworms), *Curculio* spp. (weevils), *Cyclocephala* spp. (grubs), *Cylindrocpturus adspersus* (sunflower stem weevil), *Deporaus marginatus* (mango leaf-cutting weevil), *Dermestes lardarius* (larder beetle), *Dermestes maculates* (hide beetle), *Diabrotica* spp. (chrysolemids), *Epilachna varivestis* (Mexican bean beetle), *Faustinus cubae, Hylobius pales* (pales weevil), *Hvpera* spp. (weevils), *Hypera postica* (alfalfa weevil), *Hyperdoes* spp. (Hyperodes weevil), *Hypothenemus hampei* (coffee berry beetle), *Ips* spp. (engravers), *Lasioderma serricorne* (cigarette beetle), *Leptinotarsa decemlineata* (Colorado potato beetle), *Liogenys fuscus, Liogenys suturalis, Lissorhopirus oryzophilus* (rice water weevil), *Lyctus* spp. (wood beetles/powder post beetles), *Maecolaspis joliveti, Megascelis* spp., *Melanotus communis, Meligethes* spp., *Meligethes aeneus* (blossom beetle), *Melolontha melolontha* (common European cockchafer), *Oberea brevis, Oberea linearis, Oryctes rhinoceros* (date palm beetle), *Oryzaephilus mercator* (merchant grain beetle), *Oryzaephilus surinamensis* (sawtoothed grain beetle), *Otiorhynchus* spp. (weevils), *Oulema melanopus* (cereal leaf beetle), *Oulema oryzae, Pantomorus* spp. (weevils), *Phyllophaga* spp. (May/June beetle), *Phyllophaga cuyabhana, Phyllotreta* spp. (chrysomelids), *Phynchites* spp. *Popillia japonica* (Japanese beetle), *Prostephanus truncates* (larger grain borer), *Rhizopertha dominica* (lesser grain borer), *Rhizotrogus* spp. (Eurpoean chafer), *Rhynchophorus* spp. (weevils), *Scolytus* spp. (wood beetles), *Shenophorus* spp. (Billbug), *Sitona lineatus* (pea leaf weevil), *Sitophilus* spp. (grain weevils), *Sitophilus granaries* (granary weevil), *Sitophilus oryzae* (rice weevil), *Stegobium paniceum* (drugstore beetle), *Tribolium* spp. (flour beetles), *Tribolium castaneum* (red flour beetle), *Tribolium confusum* (confused flour beetle), *Trogoderma variabile* (warehouse beetle), and *Zabrus tenebioides*.

In another embodiment, the invention disclosed in this document can be used to control Dermaptera (earwigs).

In another embodiment, the invention disclosed in this document can be used to control Dictyoptera (cockroaches). A non-exhaustive list of these pests includes, but is not limited to, *Blattella germanica* (German cockroach), *Blatta orientalis* (oriental cockroach), *Parcoblatta pennylvanica, Periplaneta americana* (American cockroach), *Periplaneta australoasiae* (Australian cockroach), *Periplanela brunnea* (brown cockroach), *Periplaneta idliginosa* (smokybrown cockroach), *Pvncoselus suninamensis* (Surinam cockroach), and *Supella longipalpa* (brownbanded cockroach).

In another embodiment, the invention disclosed in this document can be used to control Diptera (true flies). A non-exhaustive list of these pests includes, but is not limited to, *Aedes* spp (mosquitoes), *Agromyza frontella* (alfalfa blotch leafminer), *Agromyza* spp. (leaf miner flies), *Anastrepha* spp. (fruit flies), *Anastrepha suspensa* (Caribbean fruit fly), *Anopheles* spp. (mosquitoes), *Batrocera* spp. (fruit flies), *Bactrocera cucurbitae* (melon fly), *Bactrocera dorsalis* (oriental fruit fly), *Ceratitis* spp. (fruit flies), *Ceratitis capitata* (Mediterranea fruit fly), *Chrysops* spp. (deer flies), *Cochliomyia* spp. (screwworms), *Contarinia* spp. (Gall midges), *Culex* spp. (mosquitoes), *Dasineura* spp. (gall midges), *Dasineura brassicae* (cabbage gall midge), *Delia* spp., *Delia platura* (seedcorn maggot), *Drosophila* spp. (vinegar flies), *Fannia* spp. (filth flies), *Fannia canicularis* (little house fly), *Fannia scalaris* (latrine fly), *Gasterophilus intestinalis* (horse bot fly), *Gracillia perseae*, *Haematobia irritans* (horn fly), *Hylemyia* spp. (root maggots), *Hypoderma lineatum* (common cattle grub), *Liriomyza* spp. (leafminer flies), *Liriomyza brassica* (serpentine leafminer), *Melophagus ovinus* (sheep ked), *Musca* spp. (muscid flies), *Musca autumnalis* (face fly), *Musca domestica* (house fly), *Oestrus ovis* (sheep bot fly), *Oscinella frit* (frit fly), *Pegomyia betae* (beet leafminer), *Phorbia* spp., *Psila rosae* (carrot rust fly), *Rhagoletis cerasi* (cherry fruit fly), *Rhagoletis pomonella* (apple maggot), *Sitodiplosis mosellana* (orange wheat blossom midge), *Stomoxys calcitrans* (stable fly), *Tabanus* spp. (horse flies), and *Tipula* spp. (crane flies).

In another embodiment, the invention disclosed in this document can be used to control Hemiptera (true bugs). A non-exhaustive list of these pests includes, but is not limited to, *Acrosternum hilare* (green stink bug), *Blissus leucopterus* (chinch bug), *Calocoris norvegicus* (potato mirid), *Cimex hemipterus* (tropical bed bug), *Cimex lectularius* (bed bug), *Dagbertus fasciatus*, *Dichelops furcatus*, *Dysdercus suturellus* (cotton stainer), *Edessa meditabunda*, *Eurygaster maura* (cereal bug). *Euschistus heros*, *Euschistus servus* (brown stink bug), *Helopeltis antonii*, *Helopeltis theivora* (tea blight plantbug), *Lagynotomus* spp. (stink bugs), *Leptocorisa oratorius*, *Leptocorisa varicornis*, *Lygus* spp. (plant bugs), *Lygus hesperus* (western tarnished plant bug), *Maconellicoccus hirsutus*, *Neurocolpus longirostris*, *Nezara viridula* (southern green stink bug), *Phytocoris* spp. (plant bugs), *Phytocoris californicus*, *Phytocoris relativus*, *Piezodorus guildingi*, *Poecilocapsus lineatus* (fourlined plant bug), *Psallus vaccinicola*, *Pseudacysta perseae*, *Scaptocoris castanea*, and *Triatoma* spp. (bloodsucking conenose bugs/kissing bugs).

In another embodiment, the invention disclosed in this document can be used to control Homoptera (aphids, scales, whiteflies, leafhoppers). A non-exhaustive list of these pests includes, but is not limited to, *Acrythosiphon pisum* (pea aphid), *Adelges* spp. (adelgids), *Aleurodes proletella* (cabbage whitefly), *Aleurodicus disperses*, *Aleurothrixus floccosus* (woolly whitefly), *Aluacaspis* spp., *Amrasca bigutella bigutella*, *Aphrophora* spp. (leafhoppers), *Aonidiella aurantii* (California red scale), *Aphis* spp. (aphids), *Aphis gossypii* (cotton aphid), *Aphis pomi* (apple aphid), *Aulacorthun solani* (foxglove aphid), *Bemisia* spp. (whiteflies), *Bemisia argentifolii*, *Bemisia tabaci* (sweetpotato whitefly), *Brachycolus noxius* (Russian aphid), *Brachycorynella asparagi* (asparagus aphid), *Brevennia rehi*, *Brevicoryne brassicae* (cabbage aphid), *Ceroplastes* spp. (scales), *Ceroplastes rubens* (red wax scale), *Chionaspis* spp. (scales). *Chrysomphalus* spp. (scales), *Coccus* spp. (scales), *Dysaphis plantaginea* (rosy apple aphid), *Empoasca* spp. (leafhoppers), *Eriosoma lanigerum* (woolly apple aphid), *Icerya purchasi* (cottony cushion scale), *Idioscopus nitidulus* (mango leafhopper), *Laodelphax striatellus* (smaller brown planthopper), *Lepidosaphes* spp., *Macrosiphum* spp., *Macrosiphum euphorbiae* (potato aphid), *Macrosiphum granarium* (English grain aphid), *Macrosiphum rosae* (rose aphid), *Macrosteles quadrilineatus* (aster leafhopper), *Mahanarva frimbiolata*, *Metopolophium dirhodum* (rose grain aphid), *Mictis longicornis*, *Myzus persicae* (green peach aphid), *Nephotettix* spp. (leafhoppers), *Nephotettix cinctipes* (green leafhopper), *Nilaparvata lugens* (brown planthopper), *Parlatoria pergandii* (chaff scale), *Parlatoria ziziphi* (ebony scale), *Peregrinus maidis* (corn delphacid), *Philaenus* spp. (spittlebugs), *Phylloxera vitifoliae* (grape phylloxera), *Physokermes piceae* (spruce bud scale), *Planococcus* spp. (mealybugs), *Pseudococcus* spp. (mealybugs), *Pseudococcus brevipes* (pine apple mealybug), *Quadraspidiotus perniciosus* (San Jose scale), *Rhapalosiphum* spp. (aphids), *Rhapalosiphum maida* (corn leaf aphid), *Rhapalosiphum padi* (oat bird-cherry aphid), *Saissetia* spp. (scales), *Saissetia oleae* (black scale), *Schizaphis graminum* (greenbug), *Sitobion avenae* (English grain aphid), *Sogatella furcifera* (white-backed planthopper), *Therioaphis* spp. (aphids), *Toumeyella* spp. (scales), *Toxoptera* spp. (aphids), *Trialeurodes* spp. (whiteflies), *Trialeurodes vaporariorum* (greenhouse whitefly), *Trialeurodes abutiloneus* (banded-wing whitefly), *Unaspis* spp. (scales), *Unaspis yanonensis* (arrowhead scale), and *Zulia entreriana*.

In another embodiment, the invention disclosed in this document can be used to control Hymenoptera (ants, wasps, and bees). A non-exhaustive list of these pests includes, but is not limited to, *Acromyrrmex* spp., *Athalia rosae*, *Atta* spp. (leafcutting ants), *Camponotus* spp. (carpenter ants), *Diprion* spp. (sawflies), *Formica* spp. (ants), *Iridomyrmex humilis* (Argentine ant), *Monomorium* ssp., *Monomorium minumum* (little black ant), *Monomorium pharaonis* (Pharaoh ant), *Neodiprion* spp. (sawflies), *Pogonomyrmex* spp. (harvester ants), *Polistes* spp. (paper wasps), *Solenopsis* spp. (fire ants), *Tapoinoma sessile* (odorous house ant), *Tetranomorium* spp. (pavement ants), *Vespula* spp. (yellow jackets), and *Xylocopa* spp. (carpenter bees).

In another embodiment, the invention disclosed in this document can be used to control Isoptera (termites). A non-exhaustive list of these pests includes, but is not limited to, *Coptotermes* spp., *Coptotermes curvignathus*, *Coptotermes frenchii*, *Coptotermes formosanus* (Formosan subterranean termite). *Cornitermes* spp. (nasute termites), *Cryptotermes* spp. (drywood termites), *Heterotermes* spp. (desert subterranean termites), *Heterotermes aureus*, *Kalotermes* spp. (drywood termites), *Incistitermes* spp. (drywood termites). *Macrotermes* spp. (fungus growing termites), *Marginitermes* spp. (drywood termites), *Microcerotermes* spp. (harvester termites), *Microtermes obesi*, *Procornitermes* spp., *Reticulitermes* spp. (subterranean termites), *Reticulitermes banyulensis*, *Reticulitermes grassei*, *Reticulitermes flavipes* (eastern subterranean termite), *Reticulitermes hageni*, *Reticulitermes hesperus* (western subterranean termite), *Reticulitermes santonensis*, *Reticulitermes speratus*, *Reticulitermes tibialis*, *Reticulitermes virginicus*, *Schedorhinotermes* spp., and *Zootermopsis* spp. (rotten-wood termites).

In another embodiment, the invention disclosed in this document can be used to control Lepidoptera (moths and butterflies). A non-exhaustive list of these pests includes, but is not limited to, *Achoea janata*, *Adoxophyes* spp., *Adoxophyes orana*, *Agrotis* spp. (cutworms), *Agrotis ipsilon* (black cutworm), *Alabama argillacea* (cotton leafworm), *Amorbia cuneana*, *Amyelosis transitella* (navel orangeworm), *Anacamptodes defectaria*, *Anarsia lineatella* (peach twig borer), *Anomis sabulifera* (jute looper), *Anticarsia gemmatalis* (velvetbean caterpillar), *Archips argyrospila* (fruit tree leafroller), *Archips rosana* (rose leaf roller), *Argyrotaenia* spp. (tortricid moths), *Argyrotaenia citrana* (orange tortrix), *Autographa gamma, Bonagota cranaodes, Borbo cinnara* (rice leaf folder), *Bucculatrix thurberiella* (cotton leaf perforator), *Caloplilia* spp. (leaf miners), *Capua reticulana, Carposina niponensis* (peach fruit moth), *Chilo* spp., *Chlumetia transversa* (mango shoot borer), *Choristoneura rosaceana* (oblique banded leaf roller), *Chrysodeixis* spp., *Cnaphalocerus medinalis* (grass leafroller), *Colias* spp., *Conpomorpha cramerella, Cossus cossus* (carpenter moth), *Crambus* spp. (Sod webworms), *Cydia funebrana* (plum fruit moth), *Cydia molesta* (oriental fruit moth), *Cydia nignicana* (pea moth), *Cydia pomonella* (codling moth), *Darna diducta, Diaphania* spp. (stem borers), *Diatraea* spp. (stalk borers), *Diatraea saccharalis* (sugarcane borer), *Diatraea graniosella* (southwester corn borer), *Earias* spp. (bollworms), *Earias insulata* (Egyptian bollworm), *Earias vitella* (rough northern bollworm), *Ecdytopopha aurantianum, Elasmopalpus lignosellus* (lesser cornstalk borer), *Epiphysias postruttana* (light brown apple moth), *Ephestia* spp. (flour moths), *Ephestia cautella* (almond moth), *Ephestia elutella* (tobbaco moth), *Ephestia kuehniella* (Mediterranean flour moth), *Epimeces* spp., *Epinotia aporema, Erionota thrax* (banana skipper), *Eupoecilia ambiguella* (grape berry moth), *Euxoa auxiliaris* (army cutworm), *Feltia* spp. (cutworms), *Gortyna* spp. (stemborers), *Grapholita molesta* (oriental fruit moth), *Hedylepta indicata* (bean leaf webber), *Helicoverpa* spp. (noctuid moths), *Helicoverpa armigera* (cotton bollworm), *Helicoverpa zea* (bollworm/corn earworm), *Heliothis* spp. (noctuid moths), *Heliothis virescens* (tobacco budworm), *Hellula undalis* (cabbage webworm), *Indarbela* spp. (root borers), *Keiferia lycopersicella* (tomato pinworm), *Leucinodes orbonalis* (eggplant fruit borer), *Leucoptera malifoliella, Lithocollectis* spp., *Lobesia botrana* (grape fruit moth), *Loxagrotis* spp. (noctuid moths), *Loxagrotis albicosta* (western bean cutworm), *Lymantria dispar* (gypsy moth), *Lyonetia clerkella* (apple leaf miner), *Mahasena corbetti* (oil palm bagworm), *Malacosoma* spp. (tent caterpillars), *Mamestra brassicae* (cabbage armyworm), *Maruca testulalis* (bean pod borer), *Metisa plana* (bagworm), *Mythimna unipuncta* (true armyworm), *Neoleucinodes elegantalis* (small tomato borer), *Nymphula depunctalis* (rice caseworm), *Operophthera brumata* (winter moth), *Ostrinia nubilalis* (European corn borer), *Oxydia vesulia, Pandemis cerasana* (common currant tortrix), *Pandemis heparana* (brown apple tortrix), *Papilio demodocus, Pectinophora gossypiella* (pink bollworm), *Peridroma* spp. (cutworms), *Peridroma saucia* (variegated cutworm), *Perileucoptera coffeella* (white coffee leafminer), *Phthorimaea operculella* (potato tuber moth), *Phyllocnisitis citrella, Phyllonorycler* spp. (leafminers), *Pieris rapae* (imported cabbageworm), *Plathypena scabra, Plodia interpunctella* (Indian meal moth), *Plutella xylostella* (diamondback moth), *Polychrosis viteana* (grape berry moth), *Prays endocarpa, Prays oleae* (olive moth), *Pseudaletia* spp. (noctuid moths), *Pseudaletia unipunctata* (armyworm), *Pseudoplusia includens* (soybean looper), *Rachiphusia nu, Scirpophaga incertulas. Sesamia* spp. (stemborers), *Sesamia inferens* (pink rice stem borer), *Sesamia nonagrioides, Setora nitens, Sitotroga cerealella* (Angoumois grain moth), *Sparganothis pilleriana, Spodoptera* spp. (armyworms), *Spodoptera exigua* (beet armyworm), *Spodoptera fugiperda* (fall armyworm), *Spodoptera oridania* (southern armyworm), *Synanthedon* spp. (root borers). *Thecla basilides, Thermisia gemmatalis, Tineola bisselliella* (webbing clothes moth). *Trichoplusia ni* (cabbage looper), *Tuta absoluta, Yponomeuta* spp., *Zeuzera cofeae* (red branch borer), and *Zeuzera pyrina* (leopard moth).

In another embodiment, the invention disclosed in this document can be used to control Mallophaga (chewing lice). A non-exhaustive list of these pests includes, but is not limited to, *Bovicola ovis* (sheep biting louse), *Menacanthus stramineus* (chicken body louse), and *Menopon gallinea* (common hen house).

In another embodiment, the invention disclosed in this document can be used to control Orthoptera (grasshoppers, locusts, and crickets). A non-exhaustive list of these pests includes, but is not limited to, *Anabrus simplex* (Mormon cricket), *Gryllotalpidae* (mole crickets), *Locusta migratoria, Melanoplus* spp. (grasshoppers), *Microcentrum retinerve* (angular winged katydid), *Pterophylla* spp. (kaydids), *chistocerca gregaria, Scudderia furcata* (fork tailed bush katydid), and *Valanga nigricorni.*

In another embodiment, the invention disclosed in this document can be used to control Phthiraptera (sucking lice). A non-exhaustive list of these pests includes, but is not limited to, *Haematopinus* spp. (cattle and hog lice), *Linognathus ovillus* (sheep louse), *Pediculus humanus capitis* (human body louse), *Pediculus humanus humanus* (human body lice), and *Pthirus pubis* (crab louse), In another embodiment, the invention disclosed in this document can be used to control Siphonaptera (fleas). A non-exhaustive list of these pests includes, but is not limited to, *Ctenocephalides canis* (dog flea), *Ctenocephalides felis* (cat flea), and *Pulex irritans* (human flea).

In another embodiment, the invention disclosed in this document can be used to control Thysanoptera (thrips). A non-exhaustive list of these pests includes, but is not limited to, *Frankliniella fusca* (tobacco thrips), *Frankliniella occidentalis* (western flower thrips), *Frankliniella shultzei Frankliniella williamsi* (corn thrips), *Heliothrips haemorrhaidalis* (greenhouse thrips), *Riphiphorothrips cruentatus, Scirtothrips* spp., *Scirtothrips citri* (citrus thrips), *Scirtothrips dorsalis* (yellow tea thrips). *Taeniothrips rhopalantennalis*, and *Thrips* spp.

In another embodiment, the invention disclosed in this document can be used to control Thysanura (bristletails). A non-exhaustive list of these pests includes, but is not limited to, *Lepisma* spp. (silverfish) and *Thermobia* spp. (firebrats).

In another embodiment, the invention disclosed in this document can be used to control Acarina (mites and ticks). A non-exhaustive list of these pests includes, but is not limited to, *Acarapsis woodi* (tracheal mite of honeybees), *Acarus* spp. (food mites), *Acarus siro* (grain mite), *Aceria mangiferae* (mango bud mite), *Aculops* spp. *Aculops lycopersici* (tomato russet mite), *Aculops pelekasi, Aculus pelekassi, Aculus schlechtendali* (apple rust mite), *Amblyomma americanum* (lone star tick), *Boophilus* spp. (ticks), *Brevipalpus obovatus* (privet mite), *Brevipalpus phoenicis* (red and black flat mite), *Demodex* spp. (mange mites), *Dermacentor* spp. (hard ticks), *Dermacentor variabilis* (american dog tick), *Dermatophagoides pteronyssinus* (house dust mite), *Eotetranycus* spp., *Eotetranychus carpini* (yellow spider mite), *Epitimerus* spp., *Eriophyes* spp., *Ixodes* spp. (ticks), *Metatetranycus* spp., *Notoedres cati, Oligonychus* spp., *Oligonychus coffee, Oligonychus ilicus* (southern red mite), *Panonychus* spp., *Panonychus citri* (citrus red mite), *Panonychus ulmi* (European red mite), *Phyllocoptruta oleivora* (citrus rust mite), *Polyphagotarsonemun latus* (broad mite), *Rhipicephalus sanguineus* (brown dog tick), *Rhizoglyphus* spp. (bulb mites), *Sarcoptes scabiei* (itch mite), *Tegolophus perseaflorae, Tetranychus* spp., *Tetranychus urticae* (twospotted spider mite), and *Varroa destructor* (honey bee mite).

In another embodiment, the invention disclosed in this document can be used to control Nematoda (nematodes). A non-exhaustive list of these pests includes, but is not limited to, *Aphelenchoides* spp. (bud and leaf & pine wood nematodes), *Belonolaimus* spp. (sting nematodes), *Criconemella* spp. (ring nematodes), *Dirofilaria immitis* (dog heartworm), *Ditylenchus* spp. (stem and bulb nematodes), *Heterodera* spp. (cyst nematodes), *Heterodera zeae* (corn cyst nematode), *Hirschmanniella* spp. (root nematodes), *Hoplolaimus* spp. (lance nematodes), *Meloidogyne* spp. (root knot nematodes), *Meloidogyne incognita* (root knot nematode), *Onchocerca volvulus* (hook-tail worm), *Pratylenchus* spp (lesion nematodes), *Radopholus* spp. (burrowing nematodes), and *Rotylenchus reniformis* (kidney-shaped nematode).

In another embodiment, the invention disclosed in this document can be used to control Symphyla (symphylans). A non-exhaustive list of these pests includes, but is not limited to, *Scutigerella immaculata*.

For more detailed information consult "HANDBOOK OF PEST CONTROL—THE BEHAVIOR, LIFE HISTORY, AND CONTROL OF HOUSEHOLD PESTS" by Arnold Mallis, 9th Edition, copyright 2004 by GIE Media Inc.

MIXTURES

The compounds of Formula I can also be used with various insecticides, both for reasons of economy and synergy. Such insecticides include, but are not limited to, antibiotic insecticides, macrocyclic lactone insecticides (for example, avermectin insecticides, milbemycin insecticides, and spinosyn insecticides), arsenicual insecticides, botanical insecticides, carbamate insecticides (for example, benzofuranyl methylcarbamate insecticides, dimethylcarbamate insecticides, oxime carbamate insecticides, and phenyl methylcarbamate insecticides), diamide insecticides, desiccant insecticides, dinitrophenol insecticides, fluorine insecticides, formamidine insecticides, fumigant insecticides, inorganic insecticides, insect growth regulators (for example, chitin synthesis inhibitors, juvenile hormone mimics, juvenile hormones, moulting hormone agonists, moulting hormones, moulting inhibitors, precocenes, and other unclassified insect growth regulators), nereistoxin analogue insecticides, nicotinoid insecticides (for example, nitroguanidine insecticides, nitromethylene insecticides, and pyridylmethylamine insecticides), organochlorine insecticides, organophosphorus insecticides, oxadiazine insecticides, oxadiazolone insecticides, phthalimide insecticides, pyrazole insecticides, pyrethroid insecticides, pyrimidinamine insecticides, pyrrole insecticides, tetramic acid insecticides, tetronic acid insecticides, thiazole insecticides, thiazolidine insecticides, thiourea insecticides, urea insecticides, as well as, other unclassified insecticides.

Some of the particular insecticides that can be employed beneficially in combination with the compounds of Formula I include, but are not limited to, the following:—1,2-dichloropropane, abamectin, acephate, acetamiprid, acethion, acctoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluoron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cis-methrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepalléthrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide (additionally resolved isomers thereof), flucofuron, flucycloxuron, flucythrinate, flufenerim, flufenoxuron, flufenprox, fluvalinate, fonofos, formetanate, formetanate hydrochloride, formothion, formparanate, formparanate hydrochloride, fosmethilan, fospirate, fosthietan, fufenozide, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, meperfluthrin, mephosfolan, mercurous chloride, mesulfenfos, metaflumizone, methacrifos, methamidophos, methidathion, methiocarb, methocrotophos, methomyl, methoprene, methothrin, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluoron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, profluthrin, promacyl, promecarb, propaphos, propetamphos, propoxur, prothidathion, prothiofos, prothoate, protrifenbute, pymetrozine, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, tritlumuron, trimethacarb, triprene, vamidothion, vaniliprole, XMC, xylylcarb, zeta-cypermethrin, and zolaprofos.

Additionally, any combination of the above insecticides can be used.

The compounds of Formula I can also be used with herbicides and fungicides, or both for reasons of economy and synergy.

The compounds of Formula I can also be used, for reasons of economy and synergy, with acaricides, algicides, antifeedants, avicides, bactericides, bird repellents, chemosterilants, fungicides, herbicide safeners, herbicides, insect attractants, insect repellents, mammal repellents, mating disrupters, molluscicides, plant activators, plant growth regulators, rodenticides, synergists, defoliants, desiccants, disinfectants, semiochemicals, and virucides (these categories not necessarily mutually exclusive).

For more information consult "COMPENDIUM OF PESTICIDE COMMON NAMES" located at http://www.alanwood.net/pesticides/index.html. Also consult "THE PESTICIDE MANUAL" 14th Edition, edited by C D S Tomlin, copyright 2006 by British Crop Production Council.

SYNERGISTIC MIXTURES

The compounds of Formula I can be used with other compounds such as the ones mentioned under the heading "Mixtures" to form synergistic mixtures where the mode of action of the compounds in the mixtures are the same, similar, or different.

Examples of mode of actions include, but are not limited to: acetylcholine esterase inhibitor; sodium channel modulator; chitin biosynthesis inhibitor; GABA-gated chloride channel antagonist; GABA or glutamate-gated chloride channel agonist; acetylcholine receptor agonist; MET I inhibitor; $Mg^+$-stimulated ATPase inhibitor; nicotinic acetylcholine receptor agonist or antagonist; Midgut membrane disrupter; and oxidative phosphorylation disrupter.

Additionally, the following compounds are known as synergists and can be used with the invention disclosed in this document: piperonyl butoxide, piprotal, propyl isome, sesamex, sesamolin, and sulfoxide.

FORMULATIONS

A pesticide is rarely suitable for application in its pure form. It is usually necessary to add other substances so that the pesticide can be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra low volume solutions.

For further information on formulation types see "CATALOGUE OF PESTICIDE FORMULATION TYPES AND INTERNATIONAL CODING SYSTEM" Technical Monograph n°2, 5th Edition by CropLife International (2002).

Pesticides are applied most often as aqueous suspensions or emulsions prepared from concentrated formulations of such pesticides. Such water-soluble, water-suspendable, or emulsifiable formulations, are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually chosen from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and nonionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional anionic and nonionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums, may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to 3 mm. Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing, or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They are used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which, in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use this embodiment will be referred to as "OIWE".

For further information consult "INSECT PEST MANAGEMENT" 2nd Edition by D. Dent, copyright CAB International (2000). Additionally, for more detailed information consult "HANDBOOK OF PEST CONTROL—THE BEHAVIOR, LIFE HISTORY, AND CONTROL OF HOUSEHOLD PESTS" by Arnold Mallis, 9th Edition, copyright 2004 by GIE Media Inc.

OTHER FORMULATION COMPONENTS

Generally, the invention disclosed in this document when used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, antifoam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulphate; sodium dioctyl sulphosuccinate; alkyl phenol ethoxylates; and aliphatic alcohol ethoxylates.

A dispersing agent is a substance which adsorbs onto the surface of a particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulphonates. For suspension concentrates, very good adsorption and stabilization are obtained using polyelectrolytes, such as sodium naphthalene sulphonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates, In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulphonates; sodium naphthalene sulphonate formaldehyde condensates; tristyrylphenol ethoxylate phosphate esters; aliphatic alcohol ethoxylates; alky ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with 12 or more ethylene oxide units and the oil-soluble calcium salt of dodecylbenzene sulphonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilized water-insoluble materials inside the hydrophobic part of the micelle. The type of surfactants usually used for solubilization are non-ionics: sorbitan monooleates; sorbitan monooleate ethoxylates; and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alky ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, ULV formulations, and to a lesser extent granular formulations. Sometimes mixtures of solvents are used. The first main groups of solvents are aliphatic paraffinic oils such as kerosene or refined paraffins. The second main group and the most common comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are limited to, montmorillonite, e.g. bentonite; magnesium aluminum silicate; and attapulgite.

Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms cause spoilage of formulated products. Therefore preservation agents are used to eliminate or reduce their effect. Examples of such agents include, but are limited to: propionic acid and its sodium salt; sorbic acid and its sodium or potassium salts; benzoic acid and its sodium salt; p-hydroxy benzoic acid sodium salt; methyl p-hydroxy benzoate; and 1,2-benzisothiazalin-3-one (BIT).

The presence of surfactants, which lower interfacial tension, often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane while the non-silicone anti-foam agents are water-insoluble oils, such as octanol and nonanol, or silica. In both cases, the function of the anti-foam agent is to displace the surfactant from the air-water interface.

For further information see "Chemistry and Technology of Agrochemical Formulations" edited by D. A. Knowles, copyright 1998 by Kluwer Academic Publishers. Also see "Insecticides in Agriculture and Environment—Retrospects and Prospects" by A. S. Perry, I. Yamamoto, I. Ishaaya, and R. Perry, copyright 1998 by Springer-Verlag.

APPLICATIONS

The actual amount of pesticide to be applied to loci of pests is generally not critical and can readily be determined by those skilled in the art. In general, concentrations from about 0.01 grams of pesticide per hectare to about 5000 grams of pesticide per hectare are expected to provide good control.

The locus to which a pesticide is applied can be any locus inhabited by a pest, for example, vegetable crops, fruit and nut trees, grape vines, ornamental plants, domesticated animals, the interior or exterior surfaces of buildings, and the soil around buildings. Controlling pests generally means that pest populations, activity, or both, are reduced in a locus. This can come about when: pest populations are repulsed from a locus; when pests are incapacitated, partially or completely, temporarily or permanently, in or around a locus; or pests are exterminated, in whole or in part, in or around a locus. Of course a combination of these results can occur. Generally, pest populations, activity, or both are desirably reduce more than fifty percent, preferably more than 90 percent, even more preferably more than 99 percent.

Generally, with baits, the baits are placed in the ground where, for example, termites can come into contact with the bait. Baits can also be applied to a surface of a building, (horizontal, vertical, or slant, surface) where, for example, ants, termites, cockroaches, and flies, can come into contact with the bait.

Because of the unique ability of the eggs of some pests to resist pesticides repeated applications may be desirable to control newly emerged larvae.

Systemic movement of pesticides in plants may be utilized to control pests on one portion of the plant by applying the pesticides to a different portion of the plant, or to a location where the root system of a plant can uptake pesticides. For example, control of foliar-feeding insects can be controlled by drip irrigation or furrow application, or by treating the seed before planting. Seed treatment can be applied to all types of seeds, including those from which plants genetically transformed to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement and/or any other beneficial traits. Furthermore, such seed treatments with a compound or composition of the present application can further enhance the ability of a plant to better withstand stressful growing conditions. This results in a healthier, more vigorous plant, which can lead to higher yields at harvest time.

It should be readily apparent that the invention can be used with plants genetically transformed to express specialized traits, such as *Bacillus thuringiensis* or other insecticidal toxins, or those expressing herbicide resistance, or those with "stacked" foreign genes expressing insecticidal toxins, herbicide resistance, nutrition-enhancement and/or any other beneficial traits. An example of such a use is spraying such plants with the invention disclosed in this document.

The invention disclosed in this document is suitable for controlling endoparasites and ectoparasites in the veterinary medicine sector or in the field of animal keeping. Compounds according to the present application are applied in a known manner, such as by oral administration in the form of, for example, tablets, capsules, drinks, granules, by dermal application in the form of, for example, dipping, spraying, pouring on, spotting on, and dusting, and by parenteral administration in the form of, for example, an injection.

The invention disclosed in this document can also be employed advantageously in livestock keeping, for example, cattle, sheep, pigs, chickens, and geese. Suitable formulations are administered orally to the animals with the drinking water or feed. The dosages and formulations that are suitable depend on the species.

Before a pesticide can be used or sold commercially, such pesticide undergoes lengthy evaluation processes by various governmental authorities (local, regional, state, national, international). Voluminous data requirements are specified by regulatory authorities and must be addressed through data generation and submission by the product registrant or by another on the product registrant's behalf. These governmental authorities then review such data and if a determination of safety is concluded, provide the potential user or seller with product registration approval. Thereafter, in that locality where the product registration is granted and supported, such user or seller may use or sell such pesticide.

The headings in this document are for convenience only and must not be used to interpret any portion thereof. All lists herein are inclusive of any and all combinations of two or more members of the list and all ranges are inclusive of any and all subsets within the range having endpoints within the range as if each combination and subset were expressly stated herein. Unless stated otherwise or recognized by those skilled in the art as otherwise impossible, steps of processes described herein are optionally carried out in sequences different from the sequence in which the steps are discussed herein. Furthermore, steps optionally occur separately, simultaneously or with overlap in timing. For instance, such steps as heating and admixing are often separate, simultaneous, or partially overlapping in time in the art. Unless stated otherwise, when an element, material, or step capable of causing undesirable effects is present in amounts or in a form such that it does not cause the effect to an unacceptable degree it is considered substantially absent for the practice of this invention.

What is claimed is:

1. A compound according to the following formula:

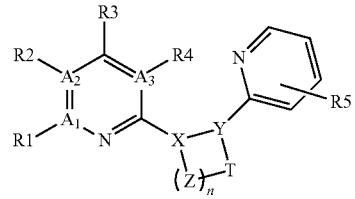

wherein
A1, A2 and A3 are each C;
X is N;
Y is C;
T is O;
Z is C(R6)$_2$ (where R6 could be the same or different);
n=2;
R1 is F, Cl, Br or I;
R2 is CN;
R3 is a substituted or unsubstituted halo-C1-C4-alkyl, wherein the halo-C1-C4-alkyl when substituted further consists of one or more substituents selected from the group consisting of F, Cl, Br, OH, CN, NO$_2$, CHO, —SCN, S(O)n-C1-C4-alkyl (where n=0-2), C1-C4-alkyl, halo-C1-C4-alkyl, C1-C4-alkylamine, C1-C4-alkoxy, halo-C1-C4 alkoxy, C1-C4-thioalkyl, halo-C1-C4-thioalkyl, C1-C4 alkylacyl, C1-C4-acyloxy, C1-C4 alkoxycarbonyl, C1-C4 alkoxy-imino, hydroxy-imino, and C1-C4-alkyl-S(O)=N;
R4 is H;
R5 is H; and
R6 is selected from the group consisting of H, substituted or unsubstituted C1-C4 alkyl, and substituted or unsubstituted aryl, wherein the C1-C4 alkyl or aryl when substituted further consists of one or more substituents selected from the group consisting of F, Cl, Br, OH, CN, NO$_2$, CHO, —SCN, S(O)n-C1-C4-alkyl (where n=0-2), C1-C4-alkyl, halo-C1-C4-alkyl, C1-C4-alkylamine, C1-C4 alkoxy, halo-C1-C4-alkoxy, C1-C4-thioalkyl, halo-C1-C4 thioalkyl, C1-C4-alkylacyl, C1-C4-acyloxy, C1-C4 alkoxycarbonyl, C1-C4-alkoxy-imino, hydroxy-imino, C1-C4-alkyl-S(O)=NH, and (C1-C4-trialkyl)Si.

2. A compound according claim 1, wherein R1 is Cl.

3. A compound according to claim 2, wherein R3 is trifluoromethyl.

4. A compound according to claim 3, wherein R6 is chosen from H, methyl, ethyl, propyl and phenyl.

5. A method of controlling insects which comprises applying to a locus where control is desired an insect-inactivating amount of a compound according to claim 1.

6. A compound according to claim 1 having the following structure

7. A compound according to claim 1 having the following structure
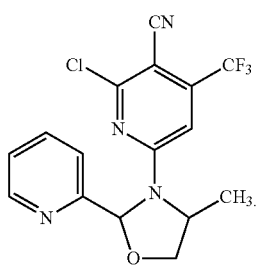 [SMILES: CC1COC(c2ccccn2)N1c1cc(C(F)(F)F)c(C#N)c(Cl)n1]
8. A compound according to claim 1 having the following structure
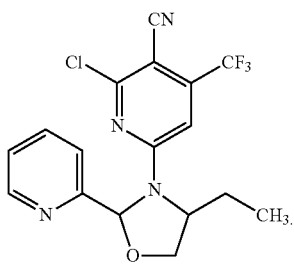 [SMILES: CCC1COC(c2ccccn2)N1c1cc(C(F)(F)F)c(C#N)c(Cl)n1]
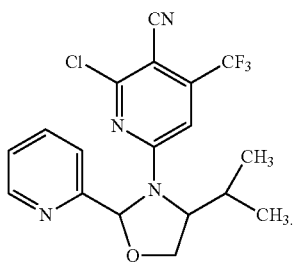 [SMILES: CC(C)C1COC(c2ccccn2)N1c1cc(C(F)(F)F)c(C#N)c(Cl)n1]
9. A compound according to claim 1 having the following structure
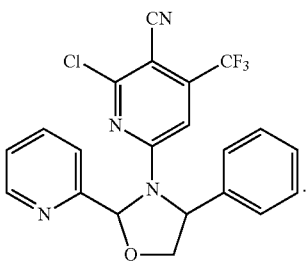 [SMILES: N#Cc1c(C(F)(F)F)cc(N2C(c3ccccc3)COC2c2ccccn2)nc1Cl]
10. A compound according to claim 1 having the following structure
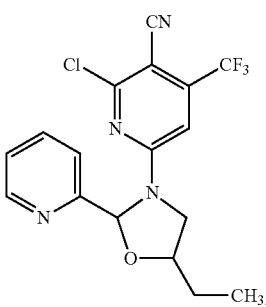 [SMILES: CCC1CN(c2cc(C(F)(F)F)c(C#N)c(Cl)n2)C(c2ccccn2)O1]
11. A compound according to claim 1, wherein R3 and R6 are unsubstituted.
* * * * *